(12) United States Patent
Locke et al.

(10) Patent No.: US 10,221,843 B2
(45) Date of Patent: Mar. 5, 2019

(54) SYSTEMS AND METHODS FOR SUPPLYING REDUCED PRESSURE AND MEASURING FLOW USING A DISC PUMP SYSTEM

(71) Applicant: KCI Licensing, Inc., San Antonio, TX (US)

(72) Inventors: Christopher Brian Locke, Bournemouth (GB); Aidan Marcus Tout, Alderbury (GB)

(73) Assignee: KCI Licensing, Inc., San Antonio, TX (US)

( * ) Notice: Subject to any disclaimer, the term of this patent is extended or adjusted under 35 U.S.C. 154(b) by 353 days.

(21) Appl. No.: 14/957,362

(22) Filed: Dec. 2, 2015

(65) Prior Publication Data

US 2016/0138582 A1 May 19, 2016

Related U.S. Application Data

(63) Continuation of application No. 13/764,510, filed on Feb. 11, 2013, now Pat. No. 9,239,059.

(Continued)

(51) Int. Cl.
*F04B 43/02* (2006.01)
*F04B 43/04* (2006.01)
(Continued)

(52) U.S. Cl.
CPC .......... *F04B 43/026* (2013.01); *F04B 43/046* (2013.01); *F04B 49/065* (2013.01);
(Continued)

(58) Field of Classification Search
CPC ...... F04B 43/04; F04B 43/046; F04B 43/047; F04B 43/06; F04B 43/065; F04B 43/0081;
(Continued)

(56) References Cited

U.S. PATENT DOCUMENTS 1,355,846 A  10/1920  Rannells
2,547,758 A   4/1951  Kelling
(Continued)

FOREIGN PATENT DOCUMENTS

AU  550575 B2  3/1986
AU  745271 B2  3/2002
(Continued)

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery.
(Continued)

*Primary Examiner* — Kenneth J Hansen

(57) ABSTRACT

Disc pump systems and methods relate to a disc pump system that includes a first disc pump having a first actuator and a second disc pump having a second actuator. The systems and methods utilize sensors to measure the displacements of the actuators and a processor to determine the pressure differential across each actuator as a function of the measured displacements of the actuators. The disc pumps are fluidly coupled by a known restriction and the processor determines the flow rate of the disc pump system based on the determined pressure differentials across each actuator and the characteristics of the known restriction.

6 Claims, 15 Drawing Sheets

Related U.S. Application Data

(60) Provisional application No. 61/604,927, filed on Feb. 29, 2012.

(51) Int. Cl.
| | |
|---|---|
| *G01F 1/36* | (2006.01) |
| *G01F 1/38* | (2006.01) |
| *G01F 1/40* | (2006.01) |
| *F04B 49/06* | (2006.01) |
| *A61M 5/142* | (2006.01) |

(52) U.S. Cl.
CPC ............... *G01F 1/36* (2013.01); *G01F 1/383* (2013.01); *G01F 1/40* (2013.01); *A61M 5/14224* (2013.01)

(58) Field of Classification Search
CPC .... F04B 43/009; F04B 43/026; F04B 43/028; F04B 2201/02; F04B 23/04; A61M 5/14224
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshl et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0012666 A1* | 1/2003 | Takeuchi .............. F04B 43/043 417/322 |
| 2003/0068231 A1* | 4/2003 | Cabuz .................. F04B 43/025 417/53 |
| 2003/0143122 A1* | 7/2003 | Sander .................. B01L 3/0268 422/503 |
| 2004/0000843 A1 | 1/2004 | East |
| 2012/0034109 A1 | 2/2012 | Tout et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |

(56) References Cited

FOREIGN PATENT DOCUMENTS

| JP | 4129536 B2 | 8/2008 |
|---|---|---|
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al; "Medical Textiles; Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.; "A Dressing Allowing Continuous Treatment of a Bicsurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Žě. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
Chinese First Office Action dated Jun. 3, 2016, corresponding to CN Application No. 201380008642X with English translation.

* cited by examiner

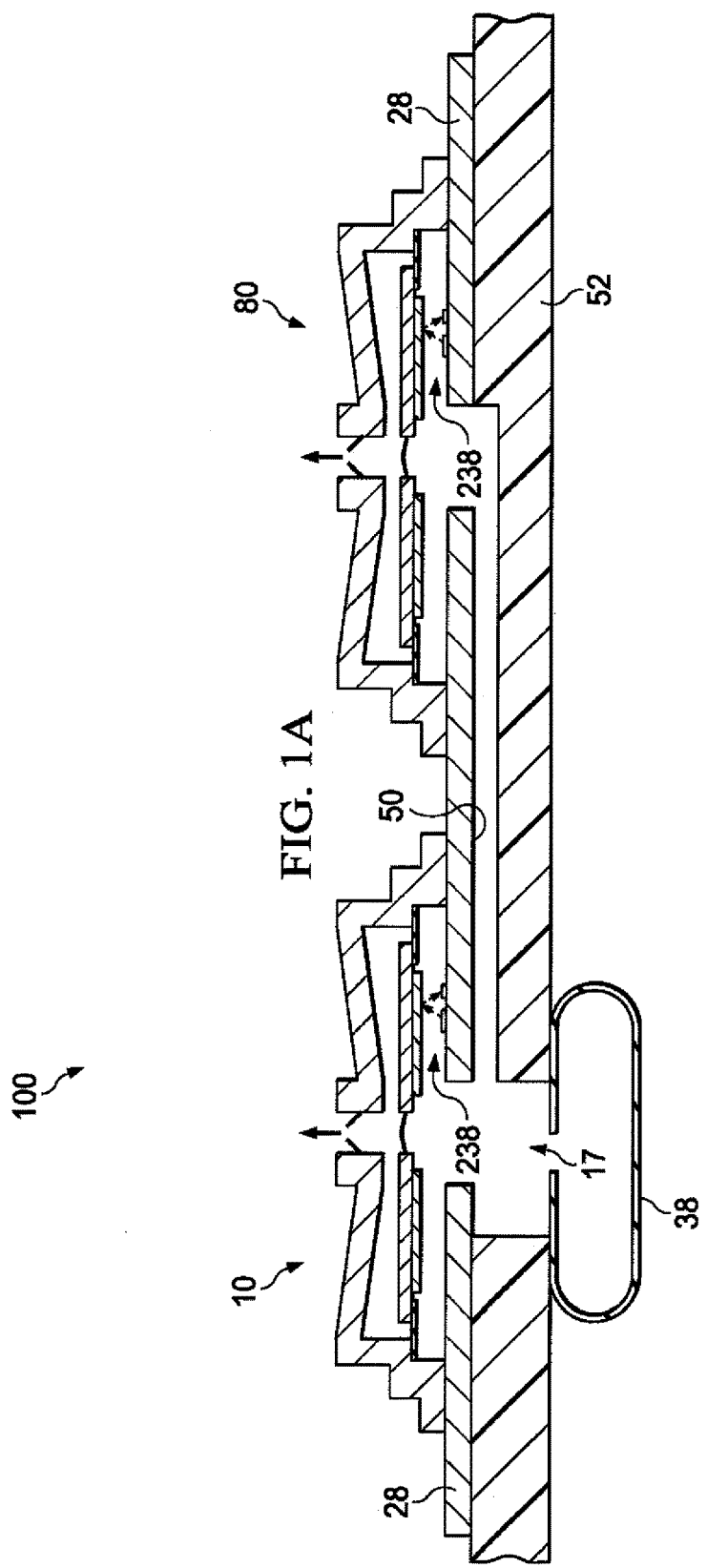

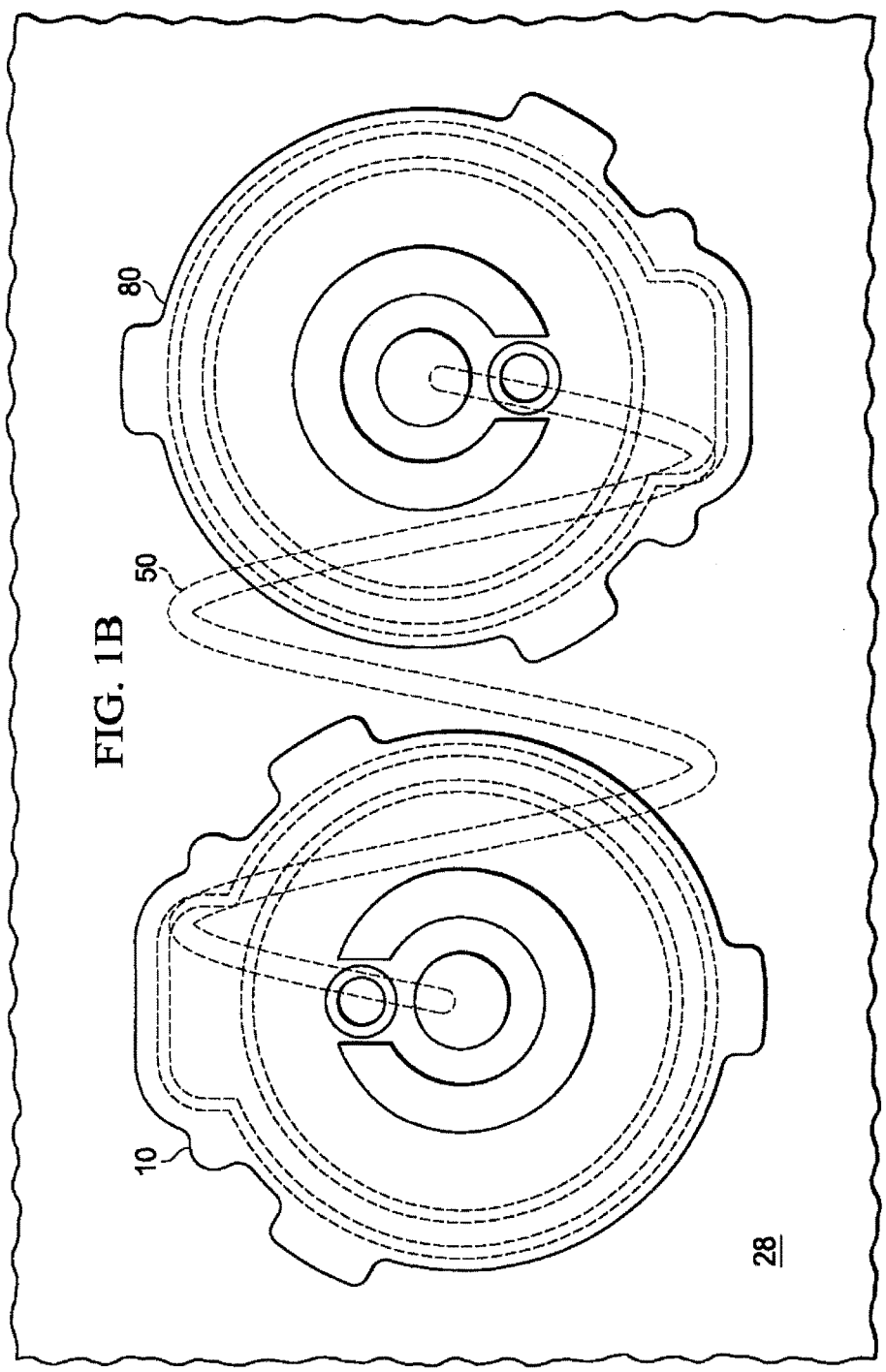

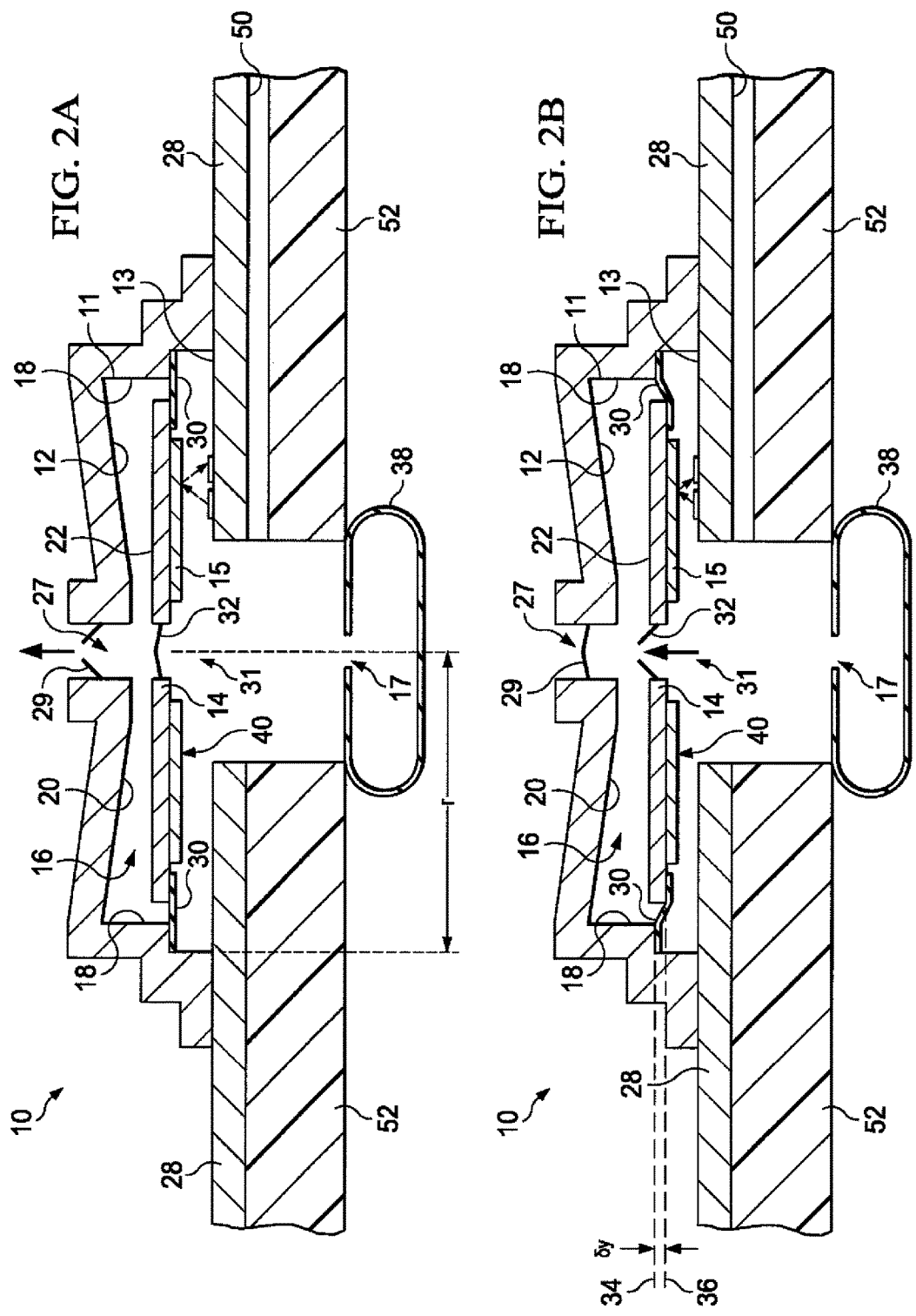

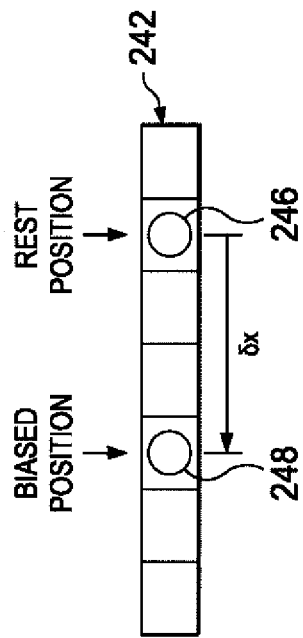
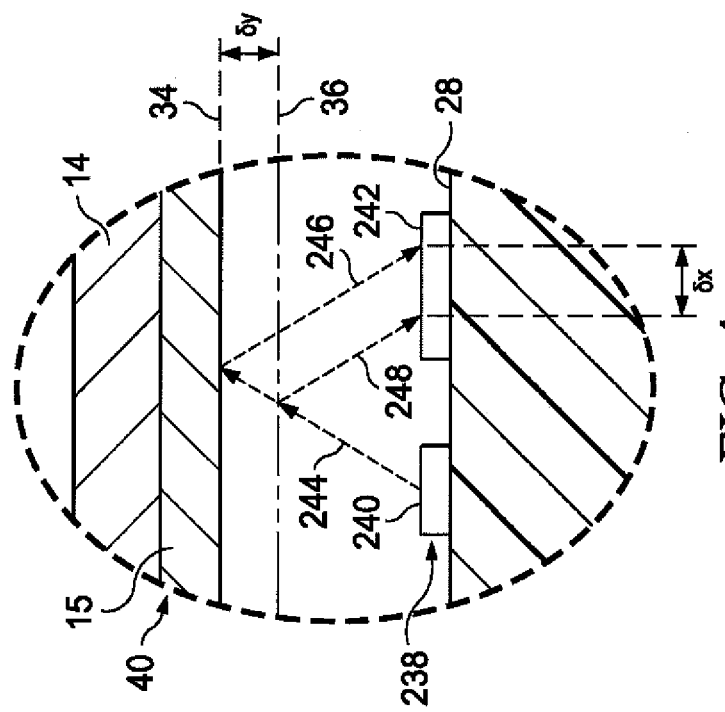

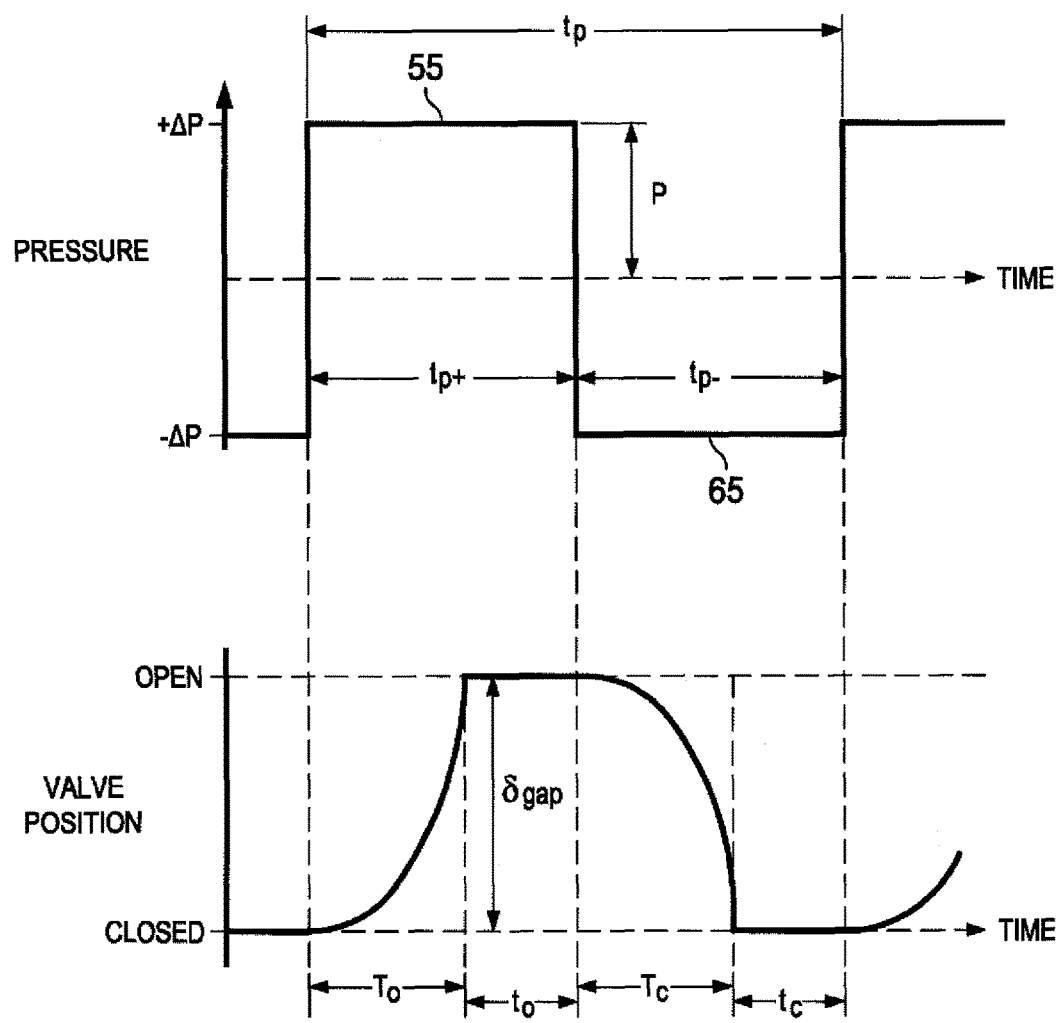

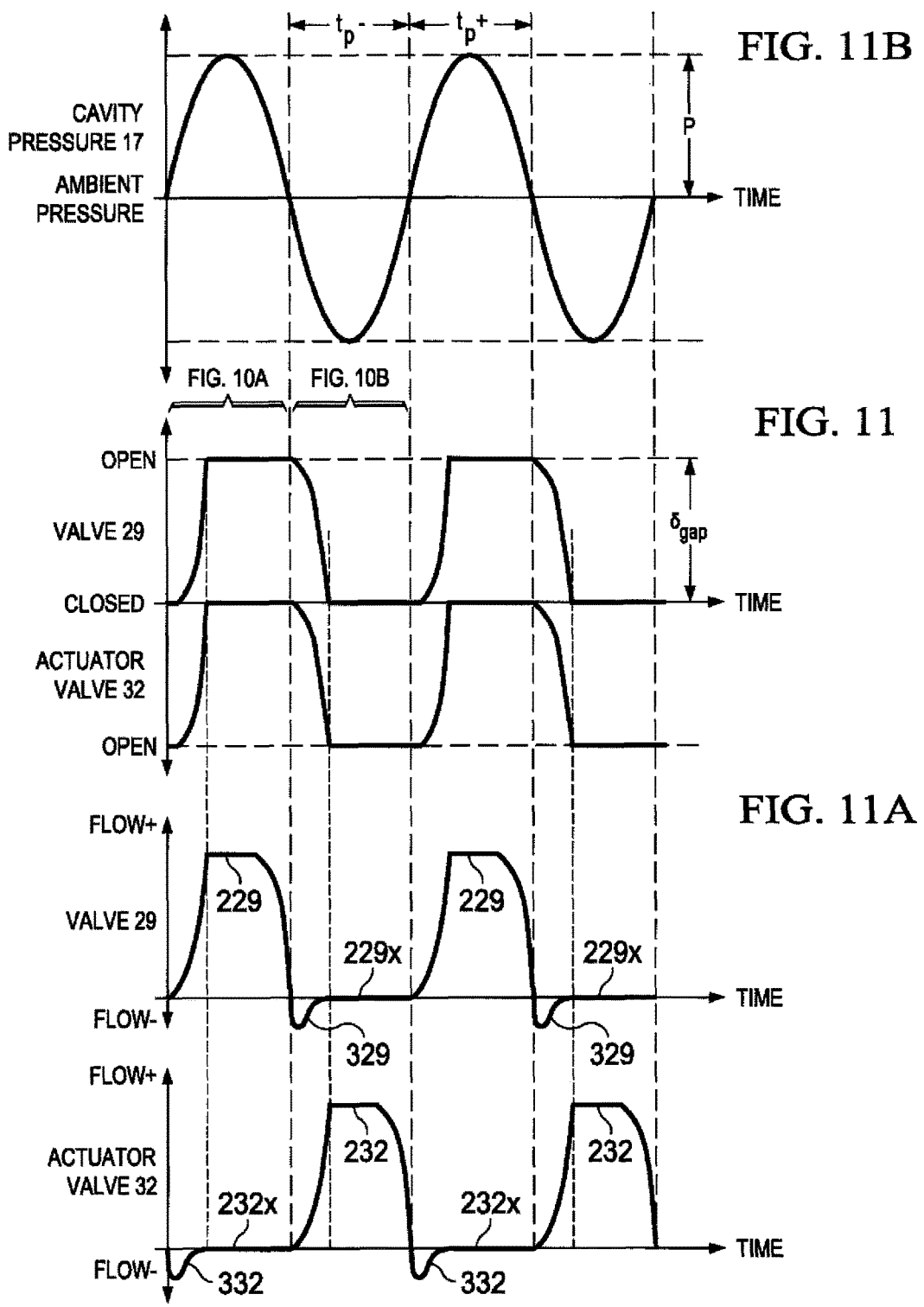

SYSTEMS AND METHODS FOR SUPPLYING REDUCED PRESSURE AND MEASURING FLOW USING A DISC PUMP SYSTEM

This application is a continuation of U.S. patent application Ser. No. 13/764,510, filed Feb. 11, 2013 which claims the benefit, under 35 USC § 119(e), of the filing of U.S. Provisional Patent Application Ser. No. 61/604,927, entitled "Systems and Methods for Supplying Reduced Pressure and Measuring Flow using a Disc Pump System," filed Feb. 29, 2012, by Locke et al., which is incorporated herein by reference for all purposes.

BACKGROUND OF THE INVENTION

1. Field of the Invention

The illustrative embodiments of the invention relate generally to a disc pump system for pumping fluid and, more specifically, to a disc pump system having two or more pumps that are fluidly coupled by a known restriction. The illustrative embodiments relate to a disc pump system that measures the pressure at each end of the known restriction to determine the flow rate of fluid pumped by the disc pump system.

2. Description of Related Art

The generation of high amplitude pressure oscillations in closed cavities has received significant attention in the fields of thermo-acoustics and disc pump type compressors. Recent developments in non-linear acoustics have allowed the generation of pressure waves with higher amplitudes than previously thought possible.

It is known to use acoustic resonance to achieve fluid pumping from defined inlets and outlets. This can be achieved using a cylindrical cavity with an acoustic driver at one end, which drives an acoustic standing wave. In such a cylindrical cavity, the acoustic pressure wave has limited amplitude. Varying cross-section cavities, such as cone, horn-cone, and bulb shapes have been used to achieve high amplitude pressure oscillations, thereby significantly increasing the pumping effect. In such high amplitude waves, the non-linear mechanisms with energy dissipation have been suppressed. However, high amplitude acoustic resonance has not been employed within disc-shaped cavities in which radial pressure oscillations are excited until recently. International Patent Application No. PCT/GB2006/001487, published as WO 2006/111775, discloses a disc pump having a substantially disc-shaped cavity with a high aspect ratio, i.e., the ratio of the radius of the cavity to the height of the cavity.

Such a disc pump has a substantially cylindrical cavity comprising a side wall closed at each end by end walls. The disc pump also comprises an actuator that drives either one of the end walls to oscillate in a direction substantially perpendicular to the surface of the driven end wall. The spatial profile of the motion of the driven end wall is described as being matched to the spatial profile of the fluid pressure oscillations within the cavity, a state described herein as mode-matching. When the disc pump is mode-matched, work done by the actuator on the fluid in the cavity adds constructively across the driven end wall surface, thereby enhancing the amplitude of the pressure oscillation in the cavity and delivering high disc pump efficiency. The efficiency of a mode-matched disc pump is dependent upon the interface between the driven end wall and the side wall.

It is desirable to maintain the efficiency of such a disc pump by structuring the interface to not decrease or dampen the motion of the driven end wall, thereby mitigating any reduction in the amplitude of the fluid pressure oscillations within the cavity.

The actuator of the disc pump described above causes an oscillatory motion of the driven end wall ("displacement oscillations") in a direction substantially perpendicular to the end wall or substantially parallel to the longitudinal axis of the cylindrical cavity, referred to hereinafter as "axial oscillations" of the driven end wall within the cavity. The axial oscillations of the driven end wall generate substantially proportional "pressure oscillations" of fluid within the cavity creating a radial pressure distribution approximating that of a Bessel function of the first kind as described in International Patent Application No. PCT/GB2006/001487, which is incorporated by reference herein. Such oscillations are referred to hereinafter as "radial oscillations" of the fluid pressure within the cavity. A portion of the driven end wall between the actuator and the side wall provides an interface with the side wall of the disc pump that decreases dampening of the displacement oscillations to mitigate any reduction of the pressure oscillations within the cavity. The portion of the driven end wall that provides such an interface is referred to hereinafter as an "isolator" as described more specifically in U.S. patent application Ser. No. 12/477,594, which is incorporated by reference herein. The illustrative embodiments of the isolator are operatively associated with the peripheral portion of the driven end wall to reduce dampening of the displacement oscillations.

Such disc pumps also have one or more valves for controlling the flow of fluid through the disc pump and, more specifically, valves being capable of operating at high frequencies. Conventional valves typically operate at lower frequencies below 500 Hz for a variety of applications. For example, many conventional compressors typically operate at 50 or 60 Hz. Linear resonance compressors that are known in the art operate between 150 and 350 Hz. Yet many portable electronic devices, including medical devices, require disc pumps for delivering a positive pressure or providing a vacuum. The disc pumps are relatively small in size, and it is advantageous for such disc pumps to be inaudible in operation to provide discrete operation. To achieve these objectives, such disc pumps must operate at very high frequencies requiring valves capable of operating at about 20 kHz and higher. To operate at these high frequencies, the valve must be responsive to a high frequency oscillating pressure that can be rectified to create a net flow of fluid through the disc pump. Such a valve is described more specifically in International Patent Application No. PCT/GB2009/050614, which is incorporated by reference herein.

Valves may be disposed in either a first or second aperture, or both apertures, for controlling the flow of fluid through the disc pump. Each valve comprises a first plate having apertures extending generally perpendicular therethrough and a second plate also having apertures extending generally perpendicular therethrough, wherein the apertures of the second plate are substantially offset from the apertures of the first plate. The valve further comprises a sidewall disposed between the first and second plate, wherein the sidewall is closed around the perimeter of the first and second plates to form a cavity between the first and second plates in fluid communication with the apertures of the first and second plates. The valve further comprises a flap disposed and moveable between the first and second plates, wherein the flap has apertures substantially offset from the apertures of the first plate and substantially aligned with the apertures of the second plate. The flap is motivated between the first and second plates in response to a change in direction of the differential pressure of the fluid across the valve.

SUMMARY

According to an illustrative embodiment, a disc pump system includes a first disc pump having a first actuator and a second disc pump having a second actuator. The disc pump system includes a substrate having a known restriction that fluidly couples the first disc pump and the second disc pump, a first optical receiver, and a second optical receiver. The first optical receiver is operable to receive a first reflected optical signal that indicates a displacement of the first actuator and to transmit a first displacement signal to a processor. The second optical receiver is operable to receive a second reflected optical signal that indicates the displacement of the second actuator and to transmit a second displacement signal to the processor. The processor is coupled to the first disc pump, the second disc pump, the first optical receiver, and the second optical receiver. The processor is configured to determine a first pressure differential across the first disc pump in response to receiving the first displacement signal, and to determine a second pressure differential across the second disc pump in response to receiving the second displacement signal. The processor is also configured to determine a fluid flow rate of the disc pump system based on the first pressure differential and the second pressure differential.

According to another illustrative embodiment, a disc pump system includes a first disc pump having a first actuator, a second disc pump having a second actuator, and a substrate having a known restriction. The first disc pump and the second disc pump are fluidly coupled by the known restriction.

A method for operating a disc pump system includes transmitting a first drive signal to a first disc pump, the first disc pump having a first actuator, and transmitting a second drive signal to a second disc pump, the second disc pump having a second actuator. The first disc pump is fluidly coupled to a load via an aperture, and the second disc pump is coupled to the aperture via a known restriction. The method includes supplying a reduced pressure to the load using the second disc pump, receiving a first displacement signal that indicates the displacement of the first actuator, and receiving a second displacement signal that indicates the displacement of the second actuator. The method further includes determining a first pressure differential across the first disc pump in response to receiving the first displacement signal and determining a second pressure differential across the second disc pump in response to receiving the second displacement signal. In addition, the method includes determining a fluid flow rate of the disc pump system based on the first pressure differential and the second pressure differential.

BRIEF DESCRIPTION OF THE DRAWINGS

FIG. 1A is a cross-section view of a disc pump system having two disc pumps fluidly coupled to a restriction passage;

FIG. 1B is a schematic, top view of the disc pump system of FIG. 1A;

FIG. 2A is a cross-section view of a first disc pump having an actuator shown in a rest position according to an illustrative embodiment;

FIG. 2B is a cross-section view of the first disc pump of FIG. 2A showing the actuator in a biased position according to an illustrative embodiment;

FIG. 4 is a detail view of a first sensor for measuring the displacement of the actuator of the first disc pump according to an illustrative embodiment;

FIG. 4A is a schematic view of an illustrative receiver of the first sensor indicating the position of the actuator when in the rest position and the biased position;

FIG. 9A shows a pressure graph of an oscillating differential pressure applied across the valve of FIG. 7A according to an illustrative embodiment;

FIG. 9B shows a fluid-flow graph of an operating cycle of the valve of FIG. 7A between an open and closed position;

FIG. 11 shows the open and closed states of the valves of the disc pump, and FIGS. 11A and 11B show the resulting flow and pressure characteristics, respectively, when the disc pump is in a free-flow mode;

DETAILED DESCRIPTION OF ILLUSTRATIVE EMBODIMENTS

Figure 3A:
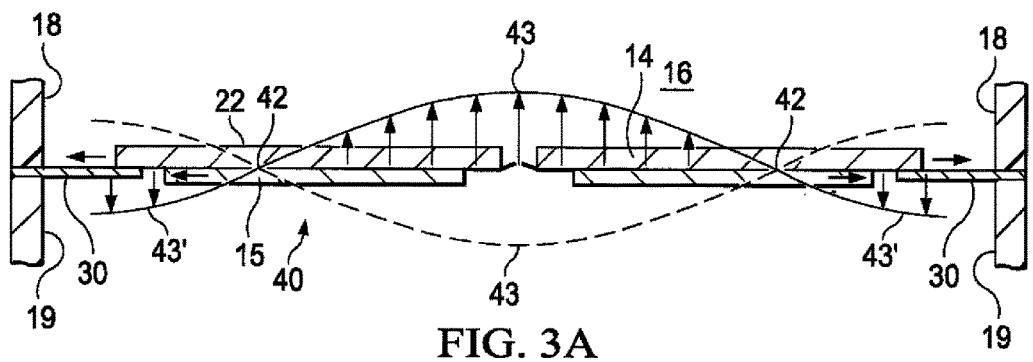
FIG. 3A shows a graph of the axial displacement oscillations for the fundamental bending mode of the actuator of the first disc pump of FIG. 2A.

In the following detailed description of several illustrative embodiments, reference is made to the accompanying drawings that form a part hereof. By way of illustration, the accompanying drawings show specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

FIG. 1A shows a disc pump system 100 having a plurality of disc pumps. The plurality of disc pumps includes at least a first disc pump 10 and a second disc pump 80 that are operable to supply a positive or negative pressure to the load 38 to pressurize or depressurize a load 38, respectively. In the illustrative embodiment of FIG. 1A, the disc pumps are mounted to a common substrate 28, such as a printed circuit board. In turn, the substrate 28 is mounted to a manifold 52 that fluidly couples the disc pumps 10, 80 to a load 38 via an aperture 17. The disc pump 10 is fluidly coupled to the aperture 17, while the disc pump 80 is fluidly coupled to the aperture 17 via a passage, such as a restriction 50, between the manifold 52 and the substrate 28. The restriction 50 may be a conduit, fluid path, or similar feature that has known dimensions and accommodates fluid flow between the disc pump 80 and the aperture 17. As such, the restriction 50 is a known restriction. In an embodiment, the restriction 50 is a cylindrical chamber of known dimensions. The cylindrical chamber may be adapted to follow a circuitous path, as shown in FIG. 1B, to lengthen the pathway of the restriction 50 and accommodate size limitations that might apply to the disc pump system 100.

Each of the disc pumps 10, 80 includes a sensor 238 to measure the pressure associated with each of the disc pumps 10, 80 at each end of the restriction 50. The difference between the pressures measured at each of the disc pumps 10, 80 is indicative of the pressure differential, or pressure drop, across the restriction. The pressure differential across the restriction 50 may be measured to determine the airflow to or from the load 38 through the aperture 17. Being able to determine the airflow through the aperture 17 facilitates control of the fluid dynamic characteristics for pressurizing or depressurizing the load 38 as the magnitude of the pressure increases or decreases at the load 38. This flow measurement data can be used to detect or locate a leak at the load 38 and to collect usage data.

The disc pumps 10, 80 may each be designed for predetermined performance characteristics to pressurize or depressurize the load 38. For example, the second disc pump 80 may be designed to deliver a higher airflow to the aperture 17 through the restriction 50 when the load 38 is at ambient pressure, while the first disc pump 10 may be designed to deliver a higher pressure differential but comparatively less airflow to the load 38. Thus, the two disc pumps 10, 80 may function as a system to optimize the fluid dynamic characteristics for pressurizing or depressurizing the load 38. The functionality of the disc pumps 10, 80 may also be reversed depending on the desired performance characteristics. That said, it is necessary to further describe the operation of the disc pumps 10, 80, which are substantially similar except for certain features of the valves that control the operational characteristics of the disc pumps 10, 80. Thus, the disc pump 10 is described in detail to point out the valve features that can be varied to achieve different flow and pressure characteristics for either one of the disc pumps 10, 80.

For the purposes of describing the functionality of features of the disc pump 10 that are illustrated in FIGS. 2A-12, the second disc pump 80 is considered to be in an off state so that the only airflow supplied to or from the load 38 is provided by the disc pump 10. In FIG. 2A, the disc pump 10 comprises a disc pump body having a substantially elliptical shape including a cylindrical wall 11 closed at each end by end plates 12, 13. The cylindrical wall 11 may be mounted to a substrate 28, which forms the end plate 13. The substrate 28 may be a printed circuit board or another suitable material. The disc pump 10 further comprises a pair of disc-shaped interior plates 14, 15 supported within the disc pump 10 by an isolator 30 having a ring-shape and affixed to the cylindrical wall 11. The internal surfaces of the cylindrical wall 11, the end plate 12, the interior plate 14, and the isolator 30 form a cavity 16 within the disc pump 10. The internal surfaces of the cavity 16 comprise a side wall 18 which is a first portion of the inside surface of the cylindrical wall 11 that is closed at both ends by end walls 20, 22 wherein the end wall 20 is the internal surface of the end plate 12 and the end wall 22 comprises the internal surface of the interior plate 14 and a first side of the isolator 30. The end wall 22 thus comprises a central portion corresponding to the inside surface of the interior plate 14 and a peripheral portion corresponding to the inside surface of the isolator 30. Although the disc pump 10 and its components are substantially elliptical in shape, the specific embodiment disclosed herein is a circular, elliptical shape.

The cylindrical wall 11 and the end plates 12, 13 may be a single component comprising the disc pump body or separate components. As shown in FIG. 2A, the end plate 13 is formed by the substrate 28 that may be a printed circuit board, an assembly board, or printed wire assembly (PWA) on which the disc pump 10 is mounted. Although the cavity 16 is substantially circular in shape, the cavity 16 may also be more generally elliptical in shape. In the embodiment shown in FIG. 2A, the end wall 20 defining the cavity 16 is shown as being generally frusto-conical. In another embodiment, the end wall 20 defining the inside surfaces of the cavity 16 may include a generally planar surface that is parallel to the actuator 40, discussed below. A disc pump comprising frusto-conical surfaces is described in more detail in the WO2006/111775 publication, which is incorporated by reference herein. The end plates 12, 13 and cylindrical wall 11 of the disc pump body may be formed from any suitable rigid material including, without limitation, metal, ceramic, glass, or plastic including, without limitation, inject-molded plastic.

The interior plates 14, 15 of the disc pump 10 together form an actuator 40 that is operatively associated with the central portion of the end wall 22, which forms the internal surfaces of the cavity 16. One of the interior plates 14, 15 must be formed of a piezoelectric material that may include any electrically active material that exhibits strain in response to an applied electrical signal, such as, for example, an electrostrictive or magnetostrictive material. In one preferred embodiment, for example, the interior plate 15 is formed of piezoelectric material that exhibits strain in response to an applied electrical signal, i.e., the active interior plate. The other one of the interior plates 14, 15 preferably possesses a bending stiffness similar to the active interior plate and may be formed of a piezoelectric material or an electrically inactive material, such as a metal or ceramic. In this embodiment, the interior plate 14 possesses a bending stiffness similar to the active interior plate 15 and is formed of an electrically inactive material, such as a metal or ceramic, i.e., the inert interior plate. When the active interior plate 15 is excited by an electrical current, the active interior plate 15 expands and contracts in a radial direction relative to the longitudinal axis of the cavity 16, causing the interior plates 14, 15 to bend, thereby inducing an axial deflection of the end walls 22 in a direction substantially perpendicular to the end walls 22 (See FIG. 3A).

In other embodiments that are not shown, the isolator 30 may support either one of the interior plates 14, 15, whether the active interior plate 15 or inert interior plate 14, from the top or the bottom surfaces depending on the specific design and orientation of the disc pump 10. In another embodiment, the actuator 40 may be replaced by a device in a force-transmitting relation with only one of the interior plates 14, 15 such as, for example, a mechanical, magnetic or electrostatic device, wherein the selected interior plate 14, 15 may be formed as an electrically inactive or passive layer of material driven into oscillation in the manner described above.

The disc pump 10 further comprises at least one aperture extending from the cavity 16 to the outside of the disc pump 10, wherein the at least one aperture contains a valve to control the flow of fluid through the aperture. The aperture may be located at any position in the cavity 16 where the actuator 40 generates a pressure differential. The embodiment of the disc pump 10 shown in FIGS. 2A-2B comprises an aperture 27 located at approximately the center of and extending through the end plate 12. The aperture 27 contains at least one end valve 29 that regulates the flow of fluid in one direction, as indicated by the arrows, so that end valve 29 functions as an outlet valve for the disc pump 10.

The disc pump 10 further comprises at least one aperture extending through the actuator 40, wherein the at least one aperture contains a valve to control the flow of fluid through the aperture. The aperture may be located at any position on the actuator 40 where the actuator 40 generates a pressure differential. The illustrative embodiment of the disc pump 10 shown in FIGS. 2A-2B, however, comprises an actuator aperture 31 located at approximately the center of and extending through the interior plates 14, 15. The actuator aperture 31 contains an actuator valve 32, which regulates the flow of fluid in one direction into the cavity 16, as indicated by the arrow, so that the actuator valve 32 functions as an inlet valve to the cavity 16. The actuator valve 32 enhances the output of the disc pump 10 by augmenting the flow of fluid into the cavity 16 and supplementing the operation of the end valve 29, as described in more detail below.

The dimensions of the cavity 16 described herein should preferably satisfy certain inequalities with respect to the relationship between the height (h) of the cavity 16 at the side wall 18 and its radius (r) which is the distance from the longitudinal axis of the cavity 16 to the side wall 18. These equations are as follows:

$r/h > 1.2$; and $h^2/r > 4 \times 10^{-10}$ meters.

In an embodiment, the ratio of the cavity radius to the cavity height (r/h) is between about 10 and about 50 when the fluid within the cavity 16 is a gas. In this example, the volume of the cavity 16 may be less than about 10 ml. Additionally, the ratio of $h^2/r$ is preferably within a range between about $10^{-6}$ and about $10^{-7}$ meters where the working fluid is a gas as opposed to a liquid.

Additionally, the cavity 16 disclosed herein should preferably satisfy the following inequality relating the cavity radius (r) and operating frequency (f), which is the frequency at which the actuator 40 vibrates to generate the axial displacement of the end wall 22. The inequality is as follows:

$$\frac{k_0(c_s)}{2\pi f} \le r \le \frac{k_0(c_f)}{2\pi f} \qquad \text{[Equation 1]}$$

wherein the speed of sound in the working fluid within the cavity 16 (c) may range between a slow speed ($c_s$) of about 115 m/s and a fast speed ($c_f$) equal to about 1,970 m/s as expressed in the equation above, and $k_0$ is a constant ($k_0$=3.83). The frequency of the oscillatory motion of the actuator 40 is preferably about equal to the lowest resonant frequency of radial pressure oscillations in the cavity 16, but may be within 20% of that value. The lowest resonant frequency of radial pressure oscillations in the cavity 16 is preferably greater than about 500 Hz.

Although it is preferable that the cavity 16 disclosed herein should satisfy individually the inequalities identified above, the relative dimensions of the cavity 16 should not be limited to cavities having the same height and radius. For example, the cavity 16 may have a slightly different shape requiring different radii or heights creating different frequency responses so that the cavity 16 resonates in a desired fashion to generate the optimal output from the disc pump 10.

In operation, the disc pump 10 may function as a source of positive pressure when the load 38 is positioned adjacent the end valve 29 to pressurize the load 38, or as a source of negative or reduced pressure when the load 38 is placed adjacent the actuator inlet valve 32 to depressurize a load 38, as illustrated by the arrows. For example, the load may be a tissue treatment system that utilizes negative pressure for treatment. The term "reduced pressure" as used herein generally refers to a pressure less than the ambient pressure where the disc pump 10 is located. Although the term "vacuum" and "negative pressure" may be used to describe the reduced pressure, the actual pressure reduction may be significantly less than the pressure reduction normally associated with a complete vacuum. The pressure is "negative" in the sense that the pressure is a gauge pressure, i.e., the pressure is reduced below ambient atmospheric pressure. Unless otherwise indicated, values of pressure stated herein are gauge pressures. References to increases in reduced pressure typically refer to a decrease in absolute pressure, while decreases in reduced pressure typically refer to an increase in absolute pressure.

As indicated above, the disc pump 10 comprises at least one actuator valve 32 and at least one end valve 29. In another embodiment, the disc pump 10 may comprise a two cavity disc pump having an end valve 29 on each side of the actuator 40.

FIG. 3A shows one possible displacement profile illustrating the axial oscillation of the driven end wall 22 of the cavity 16. The solid curved line and arrows represent the displacement of the driven end wall 22 at one point in time, and the dashed curved line represents the displacement of the driven end wall 22 one half-cycle later. The displacement as shown in this figure and the other figures is exaggerated. Because the actuator 40 is suspended by the isolator 30 and not rigidly mounted, the actuator 40 is free to oscillate about its center of mass in its fundamental mode. In this fundamental mode, the amplitude of the displacement oscillations of the actuator 40 is substantially zero at an annular displacement node 42 located between the center of the driven end wall 22 and the side wall 18. The amplitudes of the displacement oscillations at other points on the end wall 22 are greater than zero as represented by the vertical arrows. A central displacement anti-node 43 exists near the center of the actuator 40 and a peripheral displacement anti-node 43' exists near the perimeter of the actuator 40. The central displacement anti-node 43 is represented by the dashed curve after one half-cycle.

Figure 3B:
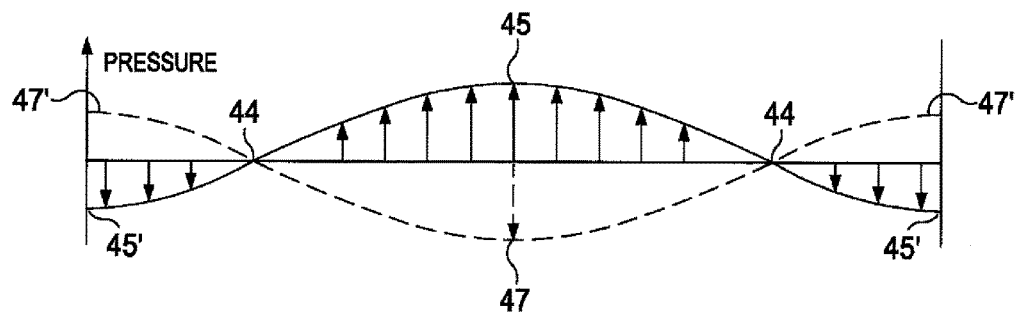
FIG. 3B shows a graph of the pressure oscillations of fluid within the cavity of the first disc pump of FIG. 2A in response to the bending mode shown in FIG. 3A.

FIG. 3B shows one possible pressure oscillation profile illustrating the pressure oscillation within the cavity 16 resulting from the axial displacement oscillations shown in FIG. 3A. The solid curved line and arrows represent the pressure at one point in time. In this mode and higher-order modes, the amplitude of the pressure oscillations has a peripheral pressure anti-node 45' near the side wall 18 of the cavity 16. The amplitude of the pressure oscillations is substantially zero at the annular pressure node 44 between the central pressure anti-node 45 and the peripheral pressure anti-node 45'. At the same time, the amplitude of the pressure oscillations as represented by the dashed line has a negative central pressure anti-node 47 near the center of the cavity 16 with a peripheral pressure anti-node 47' and the same annular pressure node 44. For a cylindrical cavity, the radial dependence of the amplitude of the pressure oscillations in the cavity 16 may be approximated by a Bessel function of the first kind. The pressure oscillations described above result from the radial movement of the fluid in the cavity 16 and so will be referred to as the "radial pressure oscillations" of the fluid within the cavity 16 as distinguished from the axial displacement oscillations of the actuator 40.

With further reference to FIGS. 3A and 3B, it can be seen that the radial dependence of the amplitude of the axial displacement oscillations of the actuator 40 (the "mode-shape" of the actuator 40) should approximate a Bessel function of the first kind so as to match more closely the radial dependence of the amplitude of the desired pressure oscillations in the cavity 16 (the "mode-shape" of the pressure oscillation). By not rigidly mounting the actuator 40 at its perimeter and allowing the actuator 40 to vibrate more freely about its center of mass, the mode-shape of the displacement oscillations substantially matches the mode-shape of the pressure oscillations in the cavity 16, thus achieving mode-shape matching or, more simply, mode-matching. Although the mode-matching may not always be perfect in this respect, the axial displacement oscillations of the actuator 40 and the corresponding pressure oscillations in the cavity 16 have substantially the same relative phase across the full surface of the actuator 40. In this embodiment, the radial position of the annular pressure node 44 of the pressure oscillations in the cavity 16 and the radial position of the annular displacement node 42 of the axial displacement oscillations of actuator 40 are substantially coincident.

As the actuator 40 vibrates about its center of mass, the radial position of the annular displacement node 42 will necessarily lie inside the radius of the actuator 40 when the actuator 40 vibrates in its fundamental bending mode as illustrated in FIG. 3A. Thus, to ensure that the annular displacement node 42 is coincident with the annular pressure node 44, the radius of the actuator ($r_{act}$) should preferably be greater than the radius of the annular pressure node 44 to optimize mode-matching. Assuming again that the pressure oscillation in the cavity 16 approximates a Bessel function of the first kind, the radius of the annular pressure node 44 would be approximately 0.63 of the radius from the center of the end wall 22 to the side wall 18, i.e., the radius of the cavity 16 ("r"), as shown in FIG. 2A. Therefore, the radius of the actuator 40 ($r_{act}$) should preferably satisfy the following inequality: $r_{act} \geq 0.63r$.

The isolator 30 may be a flexible membrane that enables the edge of the actuator 40 to move more freely, as described above, by bending and stretching in response to the vibration of the actuator 40 as shown by the displacement at the peripheral displacement anti-node 43' in FIG. 3A. The isolator 30 mitigates the potential dampening effects of the side wall 18 on the actuator 40 by providing a low mechanical impedance support between the actuator 40 and the cylindrical wall 11 of the disc pump 10, thereby reducing the dampening of the axial oscillations at the peripheral displacement anti-node 43' of the actuator 40. Essentially, the isolator 30 minimizes the energy being transferred from the actuator 40 to the side wall 18 with the outer peripheral edge of the isolator 30 remaining substantially stationary. Consequently, the annular displacement node 42 will remain substantially aligned with the annular pressure node 44 so as to maintain the mode-matching condition of the disc pump 10. Thus, the axial displacement oscillations of the driven end wall 22 continue to efficiently generate oscillations of the pressure within the cavity 16 from the central pressure anti-nodes 45, 47 to the peripheral pressure anti-nodes 45', 47' at the side wall 18 as shown in FIG. 3B.

FIG. 4 shows a sensor 238 mounted on the substrate 28, which may be a circuit board, to face the actuator 40 and measure the displacement of the actuator 40 of the disc pump 10. The sensor 238, which may also be referred to as an optical sensor, includes an optical transmitter 240 and optical receiver 242 for use in measuring displacement ($\delta y$) of the actuator 40. To measure displacement, the optical transmitter 240 communicates an optical signal 244 that may be a light wave in a visible or non-visible spectrum. The optical signal 244 is reflected off the surface of the interior plate 15 of the actuator 40 so that the reflected signal is received by the optical receiver 242, regardless of the displacement ($\delta y$) of the actuator 40, as shown in FIG. 4A. When the actuator 40 is in the rest position 34, a first reflected signal 246 impinges on the optical receiver 242 at the position shown in both FIGS. 4 and 4A. As the actuator 40 is displaced from the rest position 34 to the biased position 36, the first reflected signal 246 is displaced by a corresponding reflected displacement ($\delta x$) as a second reflected signal 248 depending on the displacement ($\delta y$) of the actuator 40. Essentially, the image of the reflected signals that impinge on the optical receiver 242 follow a path from the rest position 34 to the fully biased position 36 as shown in FIG. 4A.

The reflected displacement ($\delta x$) is proportional to the displacement ($\delta y$) of the actuator 40, which is a function of the pressure provided by the disc pump 10. More particularly, the displacement ($\delta y$) of the actuator 40 at the annular pressure node 44 is a function the difference in pressure on either side of the actuator 40. This pressure-related displacement ($\delta y$) of the actuator 40, may be viewed as a quasi-static displacement that changes gradually as the disc pump 10 supplies pressure to (or removes pressure from) the load 38. Thus, the displacements ($\delta y$) or ($\delta x$) may be measured and used to calculate the pressure differential across the actuator 40 by establishing the correlation between the pressure-related displacement ($\delta y$) of the actuator 40 and the pressure differential across the actuator 40 (and the corresponding pressure provided by the disc pump 10).

In one embodiment, the optical transmitter 240 may be a laser, a light emitting diode (LED), a vertical cavity surface emitting laser (VCSEL), or other light emitting element. The optical transmitter 240 may be positioned on the substrate 28 and oriented to reflect the optical signal 244 off any point of the interior plate 15 of the actuator 40 as long as the first reflected signal 246 and the second reflected signal 248 are received and measured by the optical receiver 242. As the actuator 40 oscillates in a fundamental mode to generate airflow as described and shown in FIG. 2A, the amplitude of the displacement oscillations of the actuator 40 may be substantially zero at any annular displacement nodes 42. Correspondingly, the amplitudes of the displacement oscillations at other points along the actuator 40 are greater than zero as also described. Therefore, the optical transmitter 240 should be positioned and oriented so that the optical signal 244 is reflected from a position close to the annular displacement node 42 to minimize the effect of the high frequency oscillations of the actuator 40 and more accurately measure the displacement (δy) of the actuator 40 as the actuator 40 moves more slowly from the rest position 34 to the biased position 36.

In one embodiment, the optical receiver 242 may include multiple pixels forming a sensor array. The optical receiver 242 may be configured to sense the position of one or more reflected beams at one or more wavelengths. As a result, the optical receiver 242 may be configured to sense the reflected displacement (δx) between the first reflected signal 246 and the second reflected signal 248. The optical receiver 242 may be configured to convert the reflected signals 246 and 248 sensed by the optical receiver 242 into electrical signals by the respective pixels of the optical receiver 242. The reflected displacement (δx) may be measured or calculated in real-time or utilizing a specified sampling frequency to determine the position of the actuator 40 relative to the substrate 28. In one embodiment, the position of the actuator 40 is computed as an average or mean position over a given time period. Pixels of the optical receiver 242 may be sized to provide additional sensitivity to detect relatively small displacements (δy) of the actuator 40 to better monitor the pressure being provided by the disc pump 10 so that the disc pump 10 can be controlled in real-time.

Alternative methods of computing the displacement of the actuator 40 may be utilized in accordance with the principles described above. It should be understood that determining the displacement of the actuator 40 may be accomplished relative to any other fixed-position element in the disc pump 10. Although generally proportional, the reflected displacement (δx) may equal the displacement (δy) of the actuator 40 multiplied by a scale factor where the scale factor may be predetermined based on the configuration of the disc pump 10 or other alignment factors. As a result, the reduced pressure within the cavity 16 of the disc pump 10 may be determined by sensing the displacement (δy) of the actuator 40 without the need for pressure sensors that directly measure the pressure provided to a load. This may be desirable because pressure sensors that directly measure pressure may be too bulky or too expensive for application in measuring the pressure provided by the disc pump 10 within a reduced pressure system for example. The illustrative embodiments optimize the utilization of space within the disc pump 10 without interfering with the pressure oscillations being created within the cavity 16 of the disc pump 10.

Figure 5A:
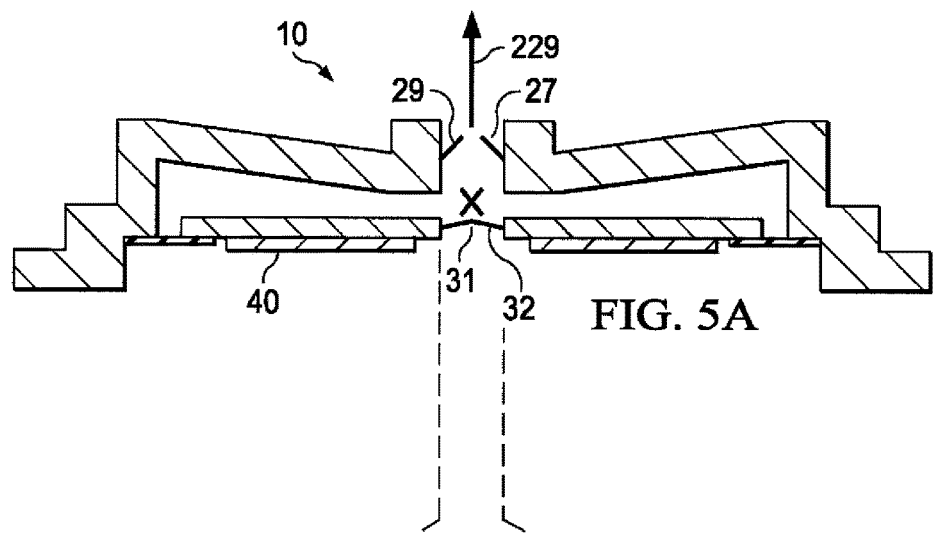
FIG. 5A is a cross-section view of the first disc pump of FIG. 2A wherein the two valves are represented by a single valve illustrated in FIGS. 7A-7D.
Figure 5B:
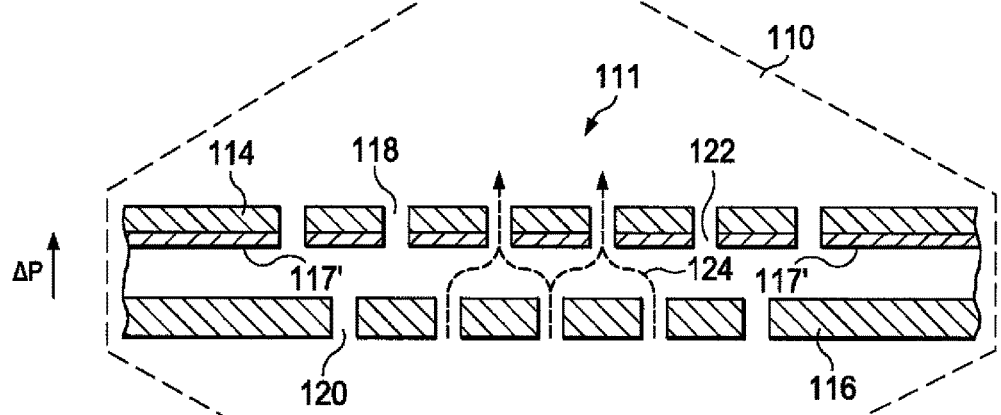
FIG. 5B is a cross-section view of a center portion of the valve of FIGS. 7A-7D.
Figure 6:
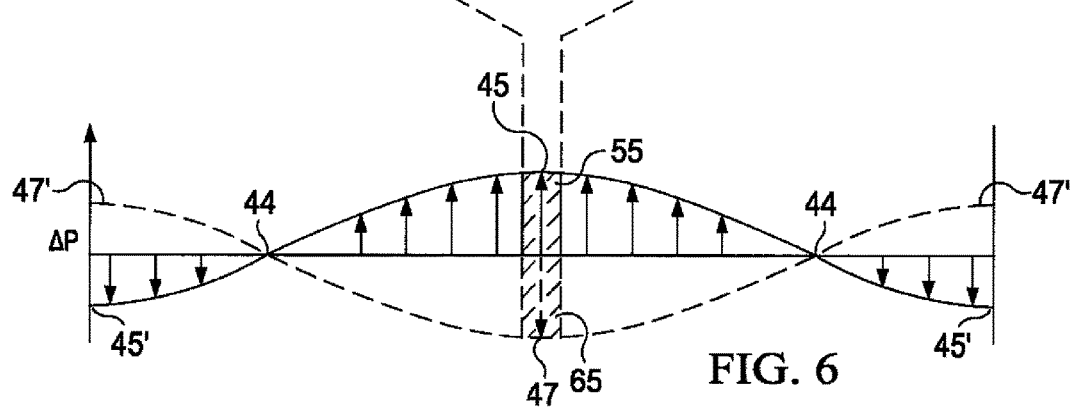
FIG. 6 shows a graph of pressure oscillations of fluid within the cavity of the first disc pump, shown in FIG. 5A, to illustrate the pressure differential applied across the valve of FIG. 5B as indicated by the dashed lines.

In FIG. 5A, the disc pump 10 of FIG. 1A is shown with the valves 29, 32, both of which are substantially similar in structure and represented, for example, by a valve 110 shown in FIGS. 7A-7D and having a center portion 111 shown in FIG. 5B. The following description associated with FIGS. 5A-9B are all based on the function of a single valve 110 that may be positioned in any one of the apertures 27, 31 of the disc pump 10. FIG. 6 shows a graph of the pressure oscillations of fluid within the disc pump 10 and shows that the valve 110 is located at or near the central pressure anti-node 45 as shown in FIG. 3B. The valve 110 allows fluid to flow in only one direction as shown in FIG. 5B. The valve 110 may be a check valve or any other valve that allows fluid to flow in only one direction. Some valve types may regulate fluid flow by switching between an open and closed position. For such valves to operate at the high frequencies generated by the actuator 40, the valves 29, 32 must have an extremely fast response time such that they are able to open and close on a timescale significantly shorter than the timescale of the pressure variation. One embodiment of the valves 29, 32 achieves this by employing an extremely light flap valve, which has low inertia and consequently is able to move rapidly in response to changes in relative pressure across the valve structure.

Referring to FIGS. 5B and 7A-D, the valve 110 is a flap valve. The valve 110 comprises a substantially cylindrical wall 112 that is ring-shaped and closed at one end by a retention plate 114 and at the other end by a sealing plate 116. The inside surface of the wall 112, the retention plate 114, and the sealing plate 116 form a cavity 115 within the valve 110. The valve 110 further comprises a substantially circular valve flap 117 disposed between the retention plate 114 and the sealing plate 116, but adjacent the sealing plate 116. The circular valve flap 117 may be disposed adjacent the retention plate 114 in another embodiment, and in this sense the valve flap 117 is considered to be "biased" against either one of the sealing plate 116 or the retention plate 114. The peripheral portion of the valve flap 117 is sandwiched between the sealing plate 116 and the wall 112 so that the motion of the valve flap 117 is restrained in the plane substantially perpendicular to the surface of the valve flap 117. The motion of the valve flap 117 in such plane may also be restrained by the peripheral portion of the valve flap 117 being attached directly to either the sealing plate 116 or the wall 112, or by the valve flap 117 being a close fit within the wall 112. The remainder of the valve flap 117 is sufficiently flexible and movable in a direction substantially perpendicular to the surface of the valve flap 117, so that a force applied to either surface of the valve flap 117 will motivate the valve flap 117 between the sealing plate 116 and the retention plate 114.

The retention plate 114 and the sealing plate 116 both have holes 118 and 120, respectively, which extend through each plate. The valve flap 117 also has holes 122 that are generally aligned with the holes 118 of the retention plate 114 to provide a passage through which fluid may flow as indicated by the dashed arrows 124 in FIGS. 5B and 8A. The holes 122 in the valve flap 117 may also be partially aligned, i.e., having only a partial overlap, with the holes 118 in the retention plate 114. Although the holes 118, 120, 122 are shown to be of substantially uniform size and shape, they may be of different diameters or even different shapes without limiting the scope of the invention. In one embodiment of the invention, the holes 118 and 120 form an alternating pattern across the surface of the plates as shown by the solid and dashed circles, respectively, in FIG. 7D. In other embodiments, the holes 118, 120, 122 may be arranged in different patterns without affecting the operation of the valve 110 with respect to the functioning of the individual pairings of holes 118, 120, 122 as illustrated by individual sets of the dashed arrows 124. The pattern of holes 118, 120, 122 may be designed to increase or decrease the number of holes to control the total flow of fluid through the valve 110 as required. For example, the number of holes 118, 120, 122 may be increased to reduce the flow resistance of the valve 110 to increase the total flow rate of the valve 110.

Figure 7A:
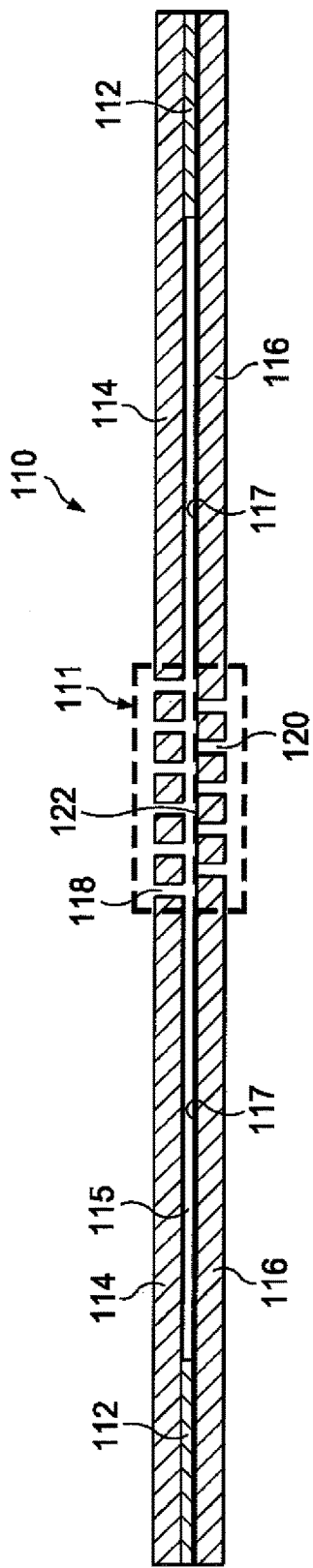
FIG. 7A is a cross-section view of an illustrative embodiment of a valve in a closed position.
Figure 7B:
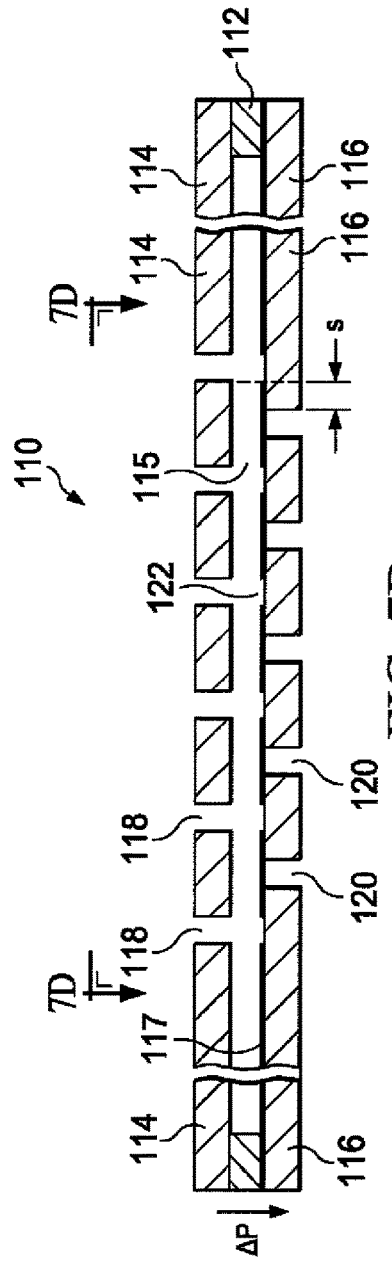
FIG. 7B is a detail, cross-section view of the valve of FIG. 7A taken along line 7B-7B in FIG. 7D.
Figure 7C:
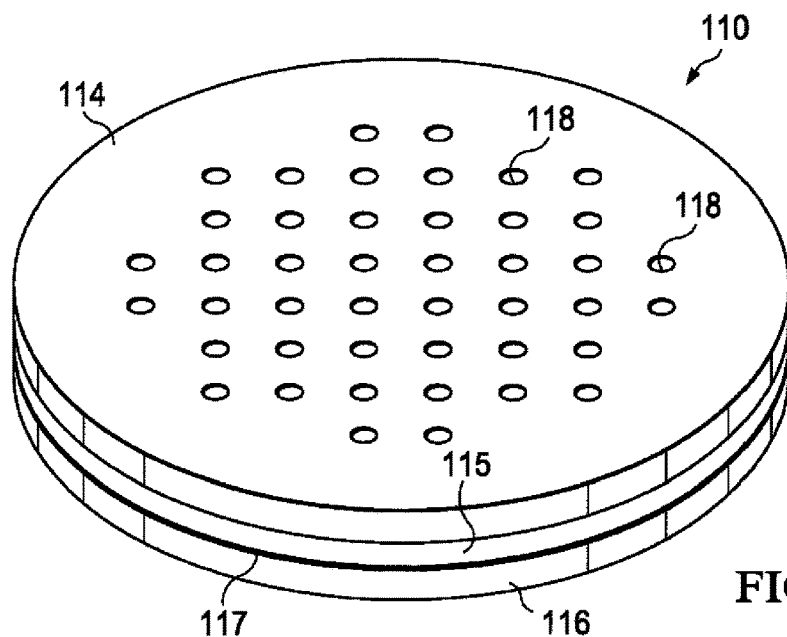
FIG. 7C is a perspective view of the valve of FIG. 7A.
Figure 7D:
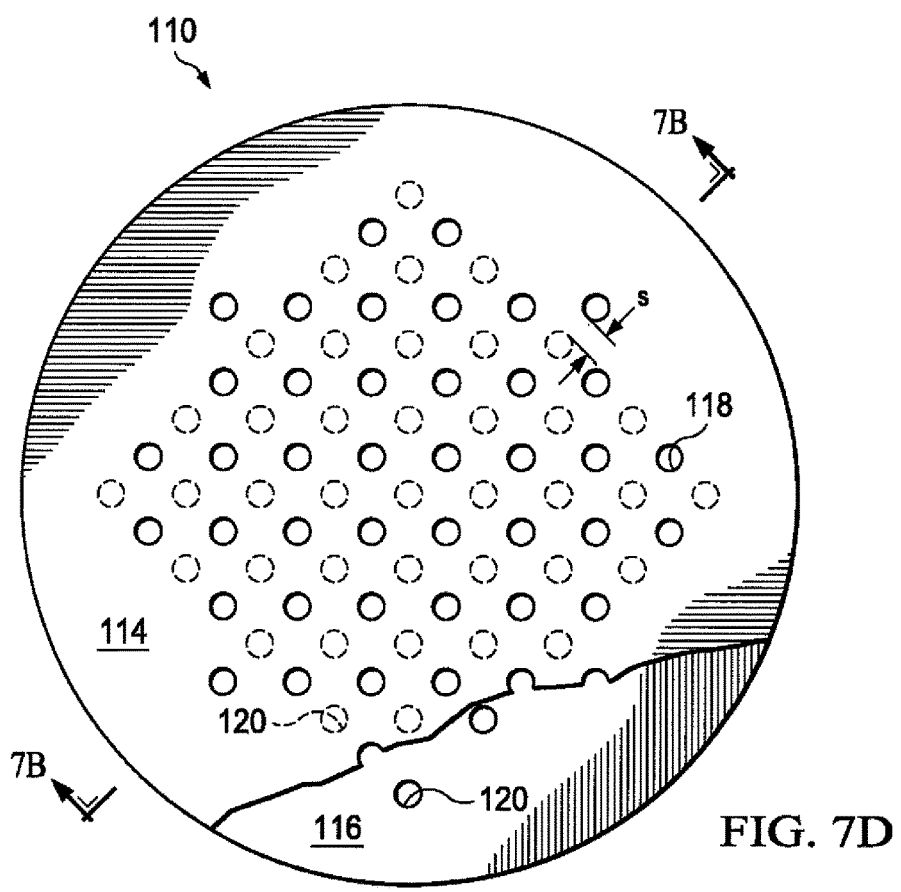
FIG. 7D is a top view of the valve of FIG. 7B.
Figure 8A:
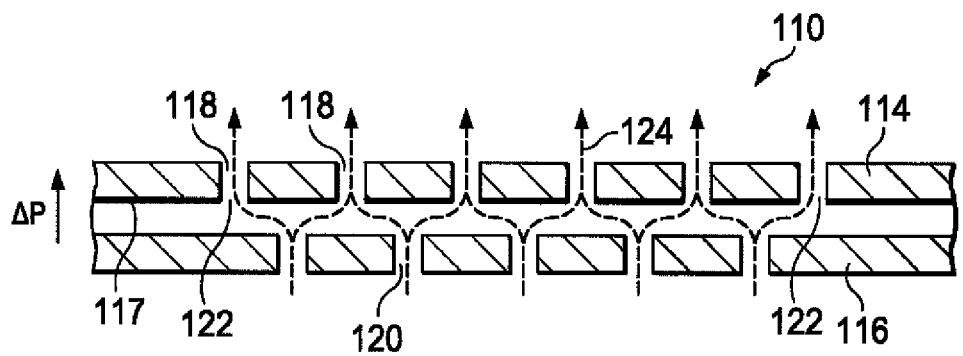
FIG. 8A shows a cross-section view of the valve in FIG. 7A in an open position when fluid flows through the valve.
Figure 8B:
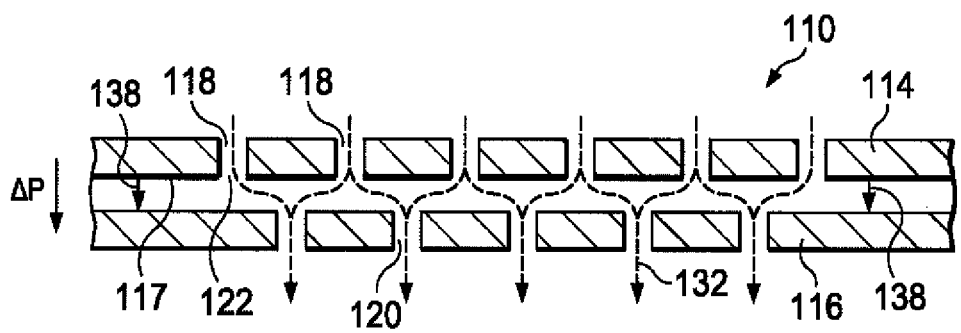
FIG. 8B shows a cross-section view of the valve in FIG. 7A in transition between the open position and a closed position.
Figure 8C:
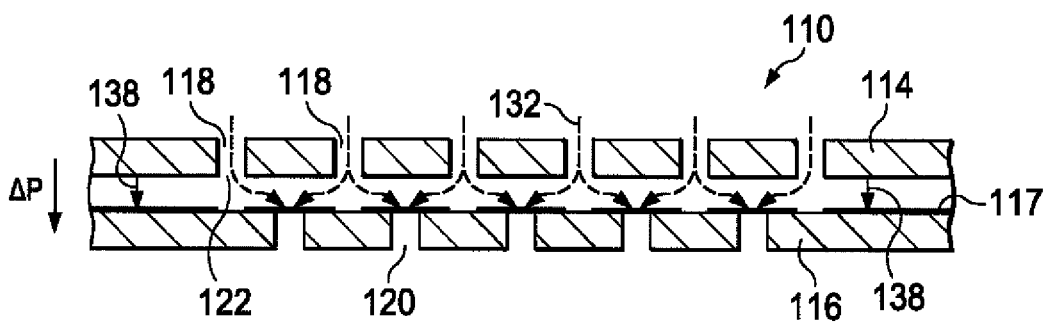
FIG. 8C shows a cross-section view of the valve of FIG. 7B in a closed position when fluid flow is blocked by a valve flap.

Referring also to FIGS. 8A-8C, the center portion 111 of the valve 110 illustrates how the valve flap 117 is motivated between the sealing plate 116 and the retention plate 114 when a force applied to either surface of the valve flap 117. When no force is applied to either surface of the valve flap 117 to overcome the bias of the valve flap 117, the valve 110 is in a "normally closed" position because the valve flap 117 is disposed adjacent the sealing plate 116 where the holes 122 of the flap are offset or not aligned with the holes 118 of the sealing plate 116. In this "normally closed" position, the flow of fluid through the sealing plate 116 is substantially blocked or covered by the non-perforated portions of the valve flap 117 as shown in FIGS. 7A and 7B. When pressure is applied against either side of the valve flap 117 that overcomes the bias of the valve flap 117 and motivates the valve flap 117 away from the sealing plate 116 towards the retention plate 114 as shown in FIGS. 5B and 8A, the valve 110 moves from the normally closed position to an "open" position over a time period, i.e., an opening time delay ($T_o$), allowing fluid to flow in the direction indicated by the dashed arrows 124. When the pressure changes direction as shown in FIG. 8B, the valve flap 117 will be motivated back towards the sealing plate 116 to the normally closed position. When this happens, fluid will flow for a short time period, i.e., a closing time delay ($T_c$), in the opposite direction as indicated by the dashed arrows 132 until the valve flap 117 seals the holes 120 of the sealing plate 116 to substantially block fluid flow through the sealing plate 116 as shown in FIG. 8C. In other embodiments of the invention, the valve flap 117 may be biased against the retention plate 114 with the holes 118, 122 aligned in a "normally open" position. In this embodiment, applying positive pressure against the valve flap 117 will be necessary to motivate the valve flap 117 into a "closed" position. Note that the terms "sealed" and "blocked" as used herein in relation to valve operation are intended to include cases in which substantial (but incomplete) sealing or blockage occurs, such that the flow resistance of the valve is greater in the "closed" position than in the "open" position.

The operation of the valve 110 is a function of the change in direction of the differential pressure ($\Delta P$) of the fluid across the valve 110. In FIG. 8B, the differential pressure has been assigned a negative value ($-\Delta P$) as indicated by the downward pointing arrow. When the differential pressure has a negative value ($-\Delta P$), the fluid pressure at the outside surface of the retention plate 114 is greater than the fluid pressure at the outside surface of the sealing plate 116. This negative differential pressure ($-\Delta P$) drives the valve flap 117 into the fully closed position as described above wherein the valve flap 117 is pressed against the sealing plate 116 to block the holes 120 in the sealing plate 116, thereby substantially preventing the flow of fluid through the valve 110. When the differential pressure across the valve 110 reverses to become a positive differential pressure ($+\Delta P$) as indicated by the upward pointing arrow in FIG. 8A, the valve flap 117 is motivated away from the sealing plate 116 and towards the retention plate 114 into the open position. When the differential pressure has a positive value ($+\Delta P$), the fluid pressure at the outside surface of the sealing plate 116 is greater than the fluid pressure at the outside surface of the retention plate 114. In the open position, the movement of the valve flap 117 unblocks the holes 120 of the sealing plate 116 so that fluid is able to flow through them and the aligned holes 122 and 118 of the valve flap 117 and the retention plate 114, respectively, as indicated by the dashed arrows 124.

When the differential pressure across the valve 110 changes from a positive differential pressure ($+\Delta P$) back to a negative differential pressure ($-\Delta P$) as indicated by the downward pointing arrow in FIG. 8B, fluid begins flowing in the opposite direction through the valve 110 as indicated by the dashed arrows 132, which forces the valve flap 117 back toward the closed position shown in FIG. 8C. In FIG. 8B, the fluid pressure between the valve flap 117 and the sealing plate 116 is lower than the fluid pressure between the valve flap 117 and the retention plate 114. Thus, the valve flap 117 experiences a net force, represented by arrows 138, which accelerates the valve flap 117 toward the sealing plate 116 to close the valve 110. In this manner, the changing differential pressure cycles the valve 110 between closed and open positions based on the direction (i.e., positive or negative) of the differential pressure across the valve 110. It should be understood that the valve flap 117 could be biased against the retention plate 114 in an open position when no differential pressure is applied across the valve 110, i.e., the valve 110 would then be in a "normally open" position.

When the differential pressure across the valve 110 reverses to become a positive differential pressure ($+\Delta P$) as shown in FIGS. 5B and 8A, the biased valve flap 117 is motivated away from the sealing plate 116 against the retention plate 114 into the open position. In this position, the movement of the valve flap 117 unblocks the holes 120 of the sealing plate 116 so that fluid is permitted to flow through them and the aligned holes 118 of the retention plate 114 and the holes 122 of the valve flap 117 as indicated by the dashed arrows 124. When the differential pressure changes from the positive differential pressure ($+\Delta P$) back to the negative differential pressure ($-\Delta P$), fluid begins to flow in the opposite direction through the valve 110 (see FIG. 8B), which forces the valve flap 117 back toward the closed position (see FIG. 8C). Thus, as the pressure oscillations in the cavity 16 cycle the valve 110 between the closed position and the open position, the disc pump 10 provides reduced pressure every half cycle when the valve 110 is in the open position.

As indicated above, the operation of the valve 110 is a function of the change in direction of the differential pressure ($\Delta P$) of the fluid across the valve 110. The differential pressure ($\Delta P$) is assumed to be substantially uniform across the entire surface of the retention plate 114 because (1) the diameter of the retention plate 114 is small relative to the wavelength of the pressure oscillations in the cavity 115, and (2) the valve 110 is located near the center of the cavity 16 where the amplitude of the positive central pressure anti-node 45 is relatively constant as indicated by the positive square-shaped portion 55 of the positive central pressure anti-node 45 and the negative square-shaped portion 65 of the negative central pressure anti-node 47 shown in FIG. 6. Therefore, there is virtually no spatial variation in the pressure across the center portion 111 of the valve 110.

FIG. 9 further illustrates the dynamic operation of the valve 110 when the valve 110 is subject to a differential pressure, which varies in time between a positive value ($+\Delta P$) and a negative value ($-\Delta P$). While in practice the time-dependence of the differential pressure across the valve 110 may be approximately sinusoidal, the time-dependence of the differential pressure across the valve 110 is approximated as varying in the square-wave form shown in FIG. 9A to facilitate explanation of the operation of the valve. The positive differential pressure 55 is applied across the valve 110 over the positive pressure time period ($t_P+$) and the negative differential pressure 65 is applied across the valve 110 over the negative pressure time period ($t_P-$) of the square wave. FIG. 9B illustrates the motion of the valve flap 117 in response to this time-varying pressure. As differential pressure ($\Delta P$) switches from negative 65 to positive 55 the valve 110 begins to open and continues to open over an opening time delay ($T_o$) until the valve flap 117 meets the retention plate 114 as also described above and as shown by the graph in FIG. 9B. As differential pressure ($\Delta P$) subsequently switches back from positive differential pressure 55 to negative differential pressure 65, the valve 110 begins to close and continues to close over a closing time delay ($T_c$) as also described above and as shown in FIG. 9B.

The retention plate 114 and the sealing plate 116 should be strong enough to withstand the fluid pressure oscillations to which they are subjected without significant mechanical deformation. The retention plate 114 and the sealing plate 116 may be formed from any suitable rigid material, such as glass, silicon, ceramic, or metal. The holes 118, 120 in the retention plate 114 and the sealing plate 116 may be formed by any suitable process including chemical etching, laser machining, mechanical drilling, powder blasting, and stamping. In one embodiment, the retention plate 114 and the sealing plate 116 are formed from sheet steel between 100 and 200 microns thick, and the holes 118, 120 therein are formed by chemical etching. The valve flap 117 may be formed from any lightweight material, such as a metal or polymer film. In one embodiment, when fluid pressure oscillations of 20 kHz or greater are present on either the retention plate side or the sealing plate side of the valve 110, the valve flap 117 may be formed from a thin polymer sheet between 1 micron and 20 microns in thickness. For example, the valve flap 117 may be formed from polyethylene terephthalate (PET) or a liquid crystal polymer film approximately 3 microns in thickness.

Figure 10A:
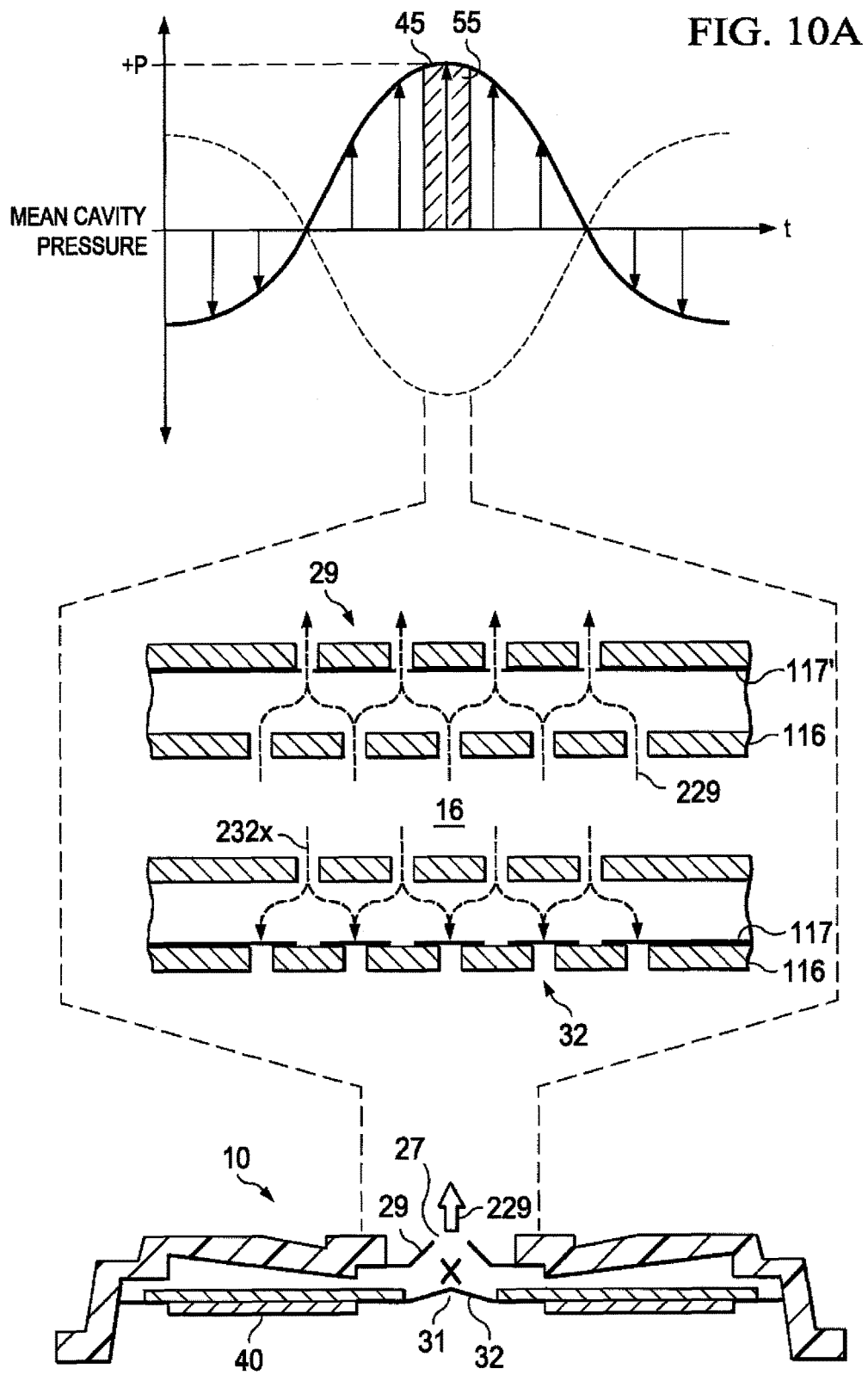
FIGS. 10A and 10B show cross-section views of the disc pump of FIG. 2A, including a view of the center portion of the valves and a graph of the positive and negative portion of an oscillating pressure wave, respectively, being applied within a cavity.
Figure 10B:
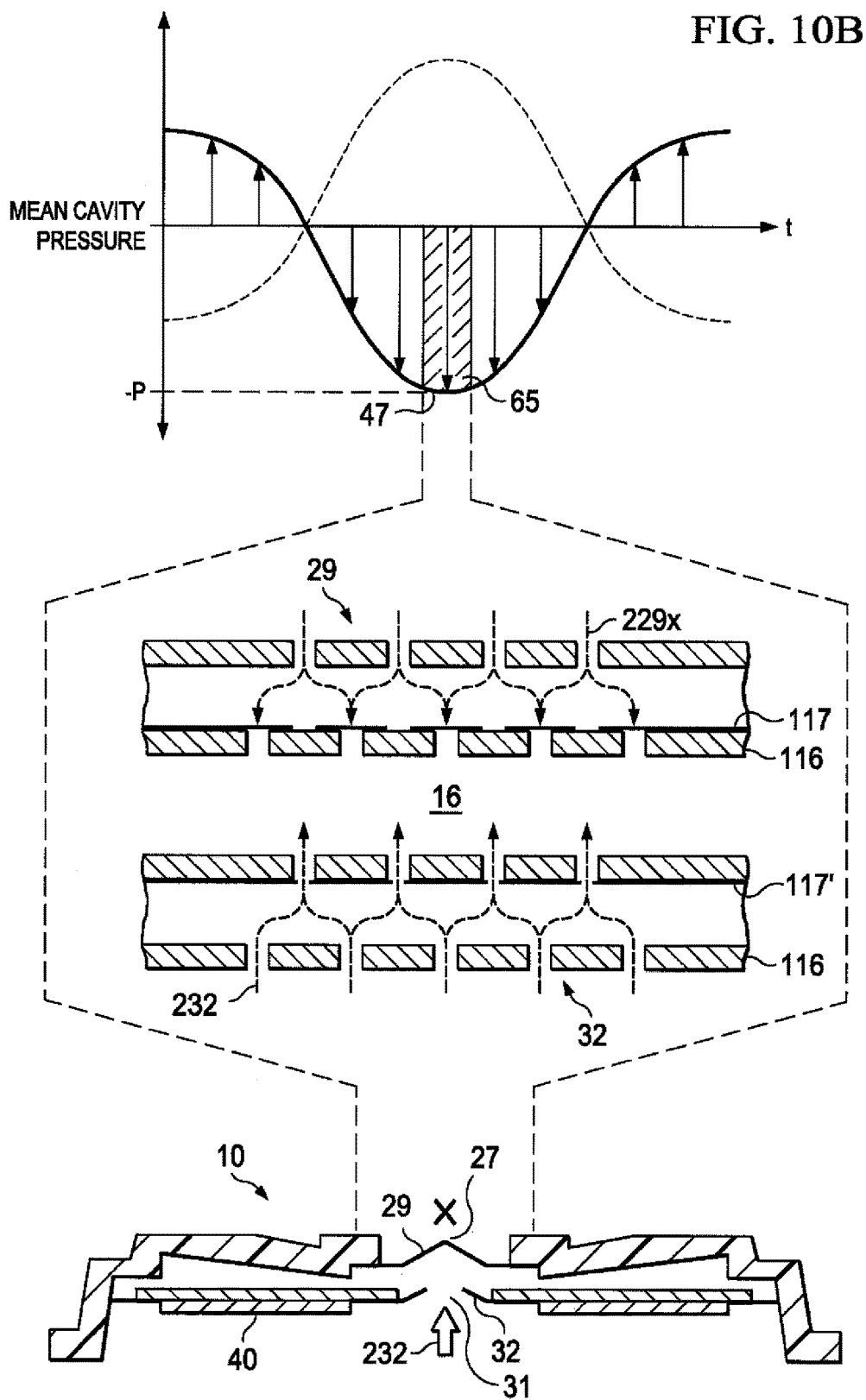

Referring now to FIGS. 10A and 10B, an exploded view of the two-valve disc pump 10 is shown that utilizes valve 110 as valves 29 and 32. In this embodiment the actuator valve 32 gates airflow 232 between the actuator aperture 31 and cavity 16 of the disc pump 10 (FIG. 10A), while end valve 29 gates airflow between the cavity 16 and the aperture 27 of the disc pump 10 (FIG. 10B). Here, aperture 27 functions as a pump outlet. Each of the figures also shows the pressure generated in the cavity 16 as the actuator 40 oscillates. Both of the valves 29 and 32 are located near the center of the cavity 16 where the amplitudes of the positive and negative central pressure anti-nodes 45 and 47, respectively, are relatively constant as indicated by the positive and negative square-shaped portions 55 and 65, respectively, as described above. In this embodiment, the valves 29 and 32 are both biased in the closed position as shown by the valve flap 117 and operate as described above when the valve flap 117 is motivated to the open position as indicated by valve flap 117'. The figures also show an exploded view of the positive and negative square-shaped portions 55, 65 of the central pressure anti-nodes 45, 47, the simultaneous impact on the operation of both valves 29, 32, and the corresponding airflow 229 and 232, respectively, generated through each one.

Referring also to the relevant portions of FIGS. 11, 11A and 11B, the open and closed states of the valves 29 and 32 (FIG. 11) and the resulting flow characteristics of each one (FIG. 11A) are shown as related to the pressure in the cavity 16 (FIG. 11B). When the actuator aperture 31 and the aperture 27 of the disc pump 10 are both at ambient pressure and the actuator 40 begins vibrating to generate pressure oscillations within the cavity 16 as described above, air begins flowing alternately through the valves 29, 32, causing air to flow from the actuator aperture 31 to the aperture 27 of the disc pump 10, i.e., the disc pump 10 begins operating in a "free-flow" mode. In one embodiment, the actuator aperture 31 of the disc pump 10 may be supplied with air at ambient pressure while the aperture 27 of the disc pump 10 is pneumatically coupled to a load (not shown) that becomes pressurized through the action of the disc pump 10. In another embodiment, the actuator aperture 31 of the disc pump 10 may be pneumatically coupled to a load (not shown) that becomes depressurized to generate a negative pressure in the load, such as a wound dressing, through the action of the disc pump 10.

The square-shaped portion 55 of the positive central pressure anti-node 45 is generated within the cavity 16 by the vibration of the actuator 40 during one half of the disc pump cycle as described above. When the actuator aperture 31 and aperture 27 of the disc pump 10 are both at ambient pressure, the square-shaped portion 55 of the positive central anti-node 45 creates a positive differential pressure across the end valve 29 and a negative differential pressure across the actuator valve 32. As a result, the actuator valve 32 begins closing and the end valve 29 begins opening so that the actuator valve 32 blocks the airflow 232x through the actuator aperture 31, while the end valve 29 opens to release air from within the cavity 16 allowing the airflow 229 to exit the cavity 16 through the aperture 27. As the actuator valve 32 closes and the end valve 29 opens (FIG. 11), the airflow 229 at the aperture 27 of the disc pump 10 increases to a maximum value dependent on the design characteristics of the end valve 29 (FIG. 11A). The opened end valve 29 allows airflow 229 to exit the disc pump cavity 16 (FIG. 11B) while the actuator valve 32 is closed. When the positive differential pressure across end valve 29 begins to decrease, the airflow 229 begins to drop until the differential pressure across the end valve 29 reaches zero. When the differential pressure across the end valve 29 falls below zero, the end valve 29 begins to close allowing some back-flow 329 of air through the end valve 29 until the end valve 29 is fully closed to block the airflow 229x, as shown in FIG. 10B.

Referring more specifically to FIG. 10B and the relevant portions of FIGS. 11, 11A, and 11B, the square-shaped portion 65 of the negative central anti-node 47 is generated within the cavity 16 by the vibration of the actuator 40 during the second half of the disc pump cycle as described above. When the actuator aperture 31 and aperture 27 of the disc pump 10 are both at ambient pressure, the square-shaped portion 65 the negative central anti-node 47 creates a negative differential pressure across the end valve 29 and a positive differential pressure across the actuator valve 32. As a result, the actuator valve 32 begins opening and the end valve 29 begins closing so that the end valve 29 blocks the airflow 229x through the aperture 27, while the actuator valve 32 opens allowing air to flow into the cavity 16 as shown by the airflow 232 through the actuator aperture 31. As the actuator valve 32 opens and the end valve 29 closes (FIG. 11), the airflow at the aperture 27 of the disc pump 10 is substantially zero except for the small amount of backflow 329 as described above (FIG. 11A). The opened actuator valve 32 allows airflow 232 into the disc pump cavity 16 (FIG. 11B) while the end valve 29 is closed. When the positive pressure differential across the actuator valve 32 begins to decrease, the airflow 232 begins to drop until the differential pressure across the actuator valve 32 reaches zero. When the differential pressure across the actuator valve 32 rises above zero, the actuator valve 32 begins to close again allowing some back-flow 332 of air through the actuator valve 32 until the actuator valve 32 is fully closed to block the airflow 232x as shown in FIG. 10A. The cycle then repeats as described above with respect to FIG. 10A. Thus, as the actuator 40 of the disc pump 10 vibrates during the two half cycles described above with respect to FIGS. 10A and 10B, the differential pressures across valves 29 and 32 cause air to flow from the actuator aperture 31 to the aperture 27 of the disc pump 10 as shown by the airflows 232, 229, respectively.

Figure 12:
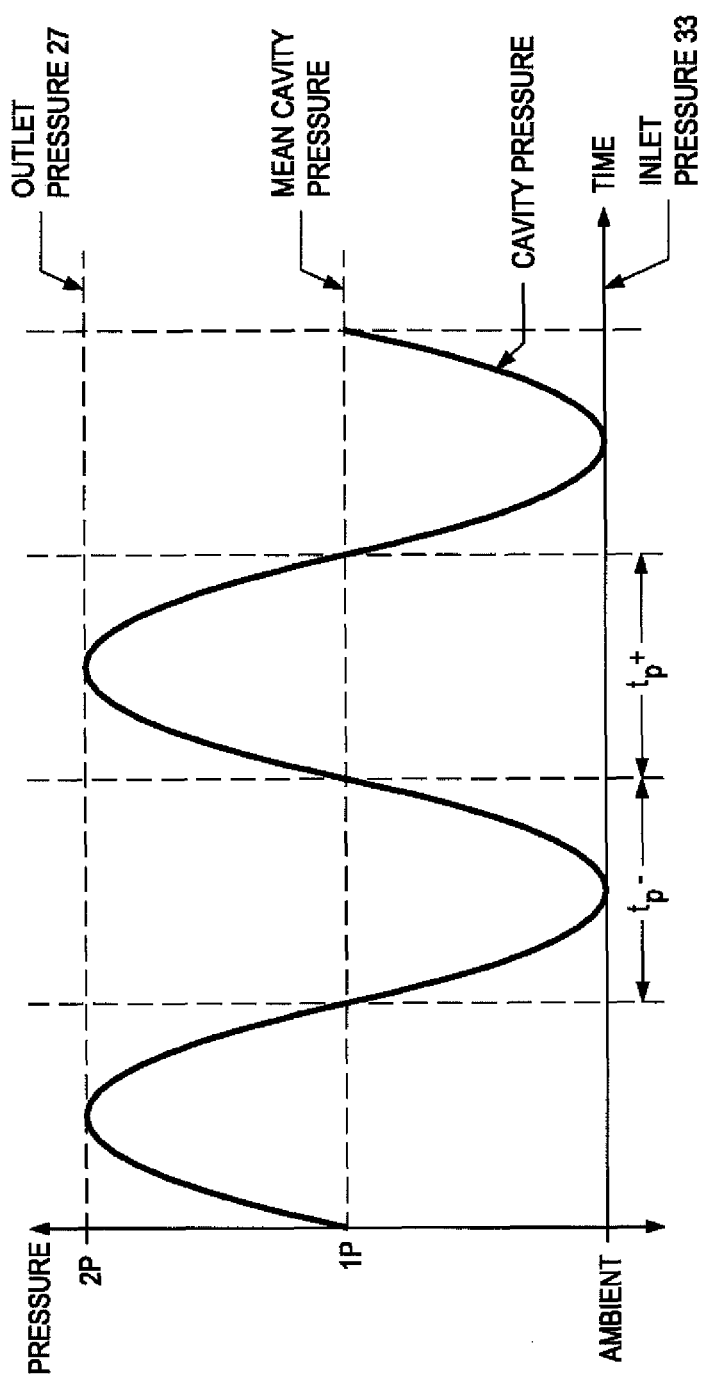
FIG. 12 shows a graph of the maximum differential pressure provided by the disc pump when the disc pump reaches the stall condition.

In the case where the actuator aperture 31 of the disc pump 10 is held at ambient pressure and the aperture 27 of the disc pump 10 is pneumatically coupled to a load that becomes pressurized through the action of the disc pump 10, the pressure at the aperture 27 of the disc pump 10 begins to increase until the aperture 27 of the disc pump 10 reaches a maximum pressure at which time the airflow from the actuator aperture 31 to the aperture 27 is negligible, i.e., the "stall" condition. FIG. 12 illustrates the pressures within the cavity 16 and outside the cavity 16 at the actuator aperture 31 and the aperture 27 when the disc pump 10 is in the stall condition. More specifically, the mean pressure in the cavity 16 is approximately 1 P above the inlet pressure (i.e. 1 P above the ambient pressure) and the pressure at the center of the cavity 16 varies between approximately ambient pressure and approximately ambient pressure plus 2 P. In the stall condition, there is no point in time at which the pressure oscillation in the cavity 16 results in a sufficient positive differential pressure across either the actuator valve 32 or end valve 29 to significantly open either valve to allow any airflow through the disc pump 10. Because the disc pump 10 utilizes two valves, the synergistic action of the two valves 29, 32 described above is capable of increasing the differential pressure between the aperture 27 and the actuator aperture 31 to a maximum differential pressure of 2 P, double that of a single valve disc pump. Thus, under the conditions described in the previous paragraph, the outlet pressure of the two-valve disc pump 10 increases from ambient in the free-flow mode to a pressure of approximately ambient plus 2 P when the disc pump 10 reaches the stall condition.

Referring again to FIGS. 1A and 1B, the disc pump system 100 includes disc pumps 10, 80 that employ the features described above with regard to FIGS. 2A-12 to supply airflow to a load 38 and measure the resulting increases or decreases in pressure at the load 38. In an illustrative implementation, the valves of the disc pumps 10, 80 are configured to provide airflow from the aperture 17 to evacuate the load 38, thereby reducing the pressure from ambient pressure, i.e., creating a negative pressure within the load 38. The load 38 may be, for example, a manifold of a negative pressure wound therapy device that provides a negative pressure to a wound to enhance healing. In a traditional implementation, one or more disc pumps are installed in parallel with a separate pressure sensor device to measure the pressure provided by both disc pumps for determining the airflow supplied to the load 38. Such pressure sensor devices are typically too bulky for wound therapy systems and difficult to integrate, as well as being a very expensive component to include in wound therapy systems. The configuration of the disc pump system 100 of FIG. 1A obviates the need for a separate pressure sensor device because each of the disc pumps 10, 80 include the integrated pressure sensors 238 described above that indirectly measure the pressure associated with each of the disc pumps 10, 80 by measuring the displacement of the actuator 40. The restriction 50 having predefined dimensions between the two disc pumps 10, 80 provides a pressure drop from which airflow may be calculated to obviate the need for a separate pressure sensor device that directly measures the pressure.

In one embodiment, the second disc pump 80 is operable to measure the displacement of its actuator 40 to determine the pressure differential associated with its actuator aperture 31. In the illustrative embodiment of FIG. 1A, the disc pumps 10, 80 are mounted to the common substrate 28 that is in turn adhered to the manifold 52. Accordingly, the restriction 50 having predetermined dimensions may be formed in the top surface of the manifold 52. As described above, the restriction 50 of FIG. 1A may be a sealed chamber formed by the underside of the substrate 28 and the manifold 52 upon which the substrate 28 is placed. The restriction 50 may be very small and may be easily fitted into a small space.

Using the system of FIG. 1A, the disc pumps 10, 80 can be used to measure the flow through the disc pump system 100 by measuring the pressure drop across the restriction 50. In one embodiment, the restriction 50 is approximated as a tube having a circular cross-section. Assuming that the flow through the restriction 50 is fully turbulent, the pressure drop may be computed based on the following equation:

$$p_1^2 - p_2^2 = \left[\lambda \frac{L}{D} * \rho_1 * \frac{\omega_1^2}{2} * \frac{T}{T_1}\right] 2 * f_1$$

Where the pipe friction coefficient is $$\frac{1}{\sqrt{\lambda}} = -2\ln\left[\frac{2.51}{\text{Re} * \sqrt{\lambda}} + \frac{\kappa}{D} * 0.269\right]$$

In the equations above, ω is the flow velocity; $p_1$ is pressure incoming; $p_2$ is pressure exiting; $T_1$ is incoming temperature of the fluid; $T_2$ is outgoing temperature of the fluid; $f_1$ is the friction coefficient of the restriction; Re is the Reynolds number; k is absolute roughness of the restriction; D is the diameter of restriction; and $\rho_2$ is density of the fluid (or incoming gas). The pipe friction coefficient varies depending on the surface of the path but is otherwise constant. Where the pressure at both the first disc pump 10 and second disc pump 80 is known, the equation above can be solved to determine the flow velocity, or flow rate. It is noted that in order for the measured flow rate to be representative of the flow provided by the disc pump system 100, one of the disc pumps 10, 80, should be temporarily stopped and used only to measure pressure (and not to provide flow).

Generally, the expected flow and associated pressure ranges provided by the disc pump system 100 are known design parameters. As such, the restriction 50 can be tuned so that measurements taken using the methodology described above will have the desired level of precision. For example, the length, diameter, and surface roughness of the restriction can be adjusted. In an exemplary embodiment, the restriction 50 may have a length of less than or equal to about 10 mm and a diameter greater than or equal to about 0.5 mm. It follows that a short, narrow, and rough restriction is best suited for a small space, but such a restriction is more likely to suffer from condensation build-up or obstruction by foreign debris. Further, the manufacturing tolerances for a smaller restriction are narrowed and more critical. A longer, wider, and smoother restriction can be manufactured more reliably and is less likely to occlude. A longer known restriction may be formed within a smaller space by arranging the known restriction in a tortuous path, as shown in FIG. 1B.

If the restriction 50 having a tortuous path is formed between the two disc pumps 10, 80 as shown in FIG. 1B, then flow through one of the disc pumps 10, 80 will need to be stopped in order to make an accurate measurement of the flow between the two disc pumps 10, 80, i.e. the measurement of the flow through the restriction 50. For the flow through one pump 10 or 80 to be representative of the flow through the disc pump system 100, it is desirable to have the disc pumps 10, 80 biased. For example, the first disc pump 10 may be biased to provide a lower flow rate that is associated with a higher pressure differential, and the second disc pump 80 may be biased to provide a higher flow rate that is associated with a lower pressure differential. In one embodiment, the second pump 80 is a high-flow pump situated at the distal end of the restriction. In the embodiment, the second disc pump 80 continues to operate when flow is measured. When the disc pumps 10, 80 are biased as described, the operation of first disc pump 10 is less critical to the operation of the disc pump system 100 when the disc pump system 100 provides increased flow (e.g., at start-up or when a leak is present). The biased disc pump configurations minimize the impact of temporarily ceasing operation of the first disc pump 10 so that the first disc pump 10 may act as a flow sensor because second disc pump 80 provides the majority of the flow. Conversely, when the load 38 is evacuated and an increased pressure differential is desired, the high-flow biased second disc pump 80 can be switched off and the high-pressure first disc pump 10 can function while the flow rate is measured.

Figure 13:
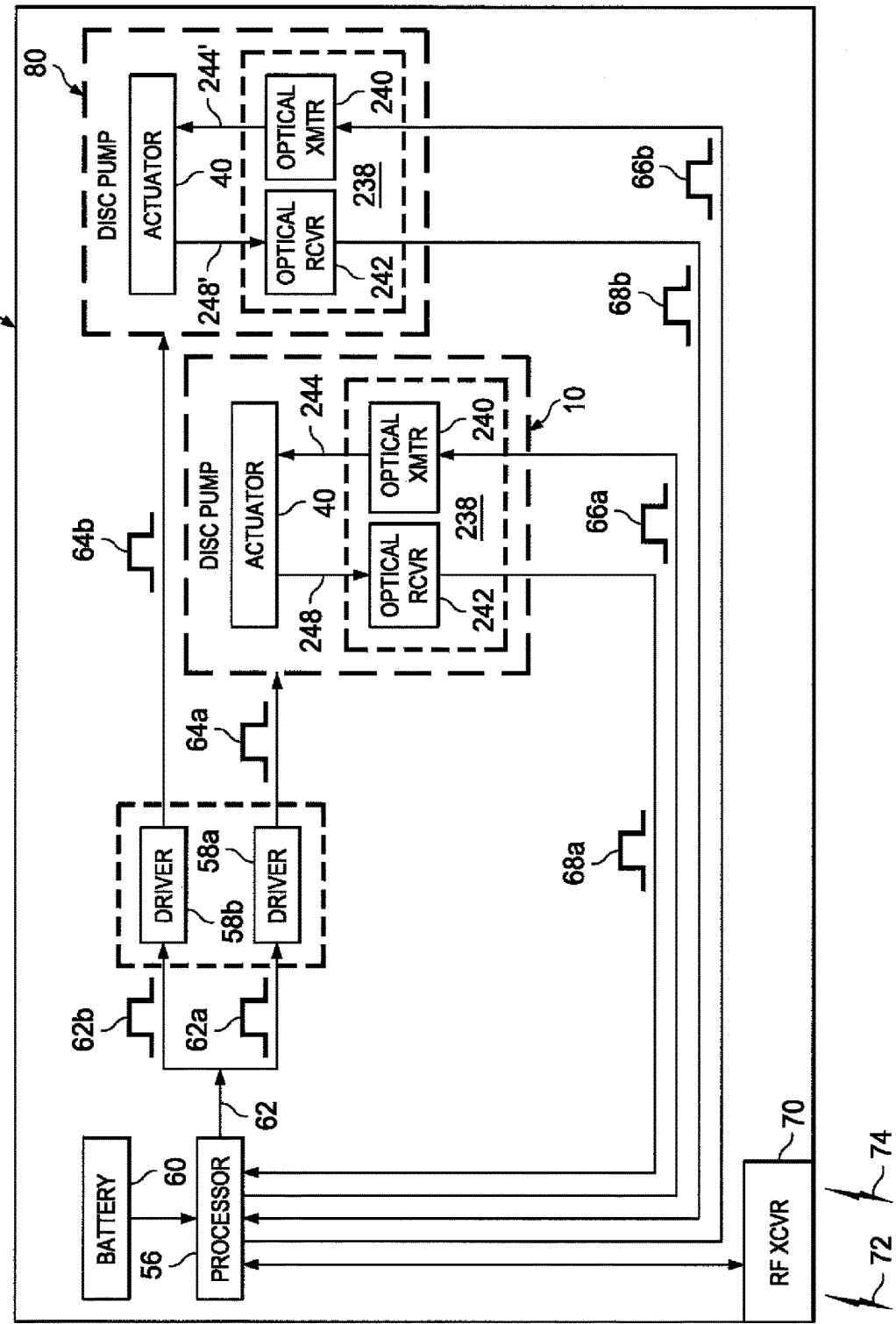
FIG. 13 is a block diagram of an illustrative circuit of a disc pump system for measuring and controlling a reduced pressure generated by the disc pump system.

FIG. 13 is a block diagram that illustrates the functionality of the disc pump system of FIG. 1A. The disc pump system 100 includes a first disc pump 10 and second disc pump 80. Each of the disc pumps 10, 80 includes an sensor 238 that is operable to measure the displacement of an actuator 40, as described above with regard to FIG. 4. It should be understood that other sensors may also be utilized as part of the disc pump system 100 in the place of the sensors 238. The disc pump system 100 comprises a battery 60 to power the disc pump system 100. The elements of the disc pump system 100 are interconnected and communicate through wires, paths, traces, leads, and other conductive elements. The disc pump system 100 also includes a controller or processor 56 and a driver 58 that may comprise two distinct drivers 58a, 58b. The processor 56 is adapted to communicate with the driver 58. The driver 58 is functional to receive a control signal 62 from the processor 56. The control signal 62 may include two distinct control signals 62a, 62b. The driver 58 generates a first drive signal 64a that energizes the actuator 40 in the first disc pump 10 and a second drive signal 64b that energizes the actuator 40 in the second disc pump 80. In an alternative embodiment, the processor communicates first and second control signals 62a, 62b, to first and second drivers 58a, 58b, respectively. The first and second drivers 58a, 58b then generate first and second drive signals 64a and 64b to energize the actuators 40 of the disc pumps 10, 80. The first and second control signals 62a, 62b and the corresponding drive signals 64a, 64b may be the same or different.

The processor 56 may also provide illumination signals 66a, 66b to the optical transmitters 240 for illuminating the actuators 40 with optical signals 244. The optical signals 244 are reflected by the actuators 40 to the optical receivers 242 as illustrated by the reflected signals 248, which are also described above with regard to FIGS. 4 and 4A. When the reflected signals 248 impinge on the optical receivers 242, the optical receivers 242 provide displacement signals 68a, 68b to the processor 56 that correspond to the displacement ($\delta y$) of the actuators 40. The processor 56 is configured to calculate the pressure generated by each of the disc pumps 10, 80 at the load 38 as a function of the displacement ($\delta y$) of the actuator 40 as represented by the displacement signal 68a, 68b. In one embodiment, the processor 56 may be configured to average a plurality of reflected signals 248 to determine average displacements of the actuator 40 over time. In another embodiment, the processor 56 may utilize the displacement signals 68a, 68b as feedback to adjust the control signal 62 and corresponding drive signals 64a, 64b for regulating the pressure at the load 38. In one embodiment, the processor 56 calculates the flow rate provided by the disc pump system 100 as a function of the determined pressures generated at each of the disc pumps 10, 80, as described above.

The processor 56, driver 58, and other control circuitry of the disc pump system 100 may be referred to as an electronic circuit. The processor 56 may be circuitry or logic enabled to control the disc pumps 10, 80. The processor 56 may function as or comprise microprocessors, digital signal processors, application-specific integrated circuits (ASIC), central processing units, digital logic or other devices suitable for controlling an electronic device including one or more hardware and software elements, executing software, instructions, programs, and applications, converting and processing signals and information, and performing other related tasks. The processor 56 may be a single chip or integrated with other computing or communications elements. In one embodiment, the processor 56 may include or communicate with a memory. The memory may be a hardware element, device, or recording media configured to store data for subsequent retrieval or access at a later time. The memory may be static or dynamic memory in the form of random access memory, cache, or other miniaturized storage medium suitable for storage of data, instructions, and information. In an alternative embodiment, the electronic circuit may be analog circuitry that is configured to perform the same or analogous functionality for measuring the pressure and controlling the displacement of the actuators 40 in the cavities of the disc pumps 10, 80, as described above.

The disc pump system 100 may also include an RF transceiver 70 for communicating information and data relating to the performance of the disc pump system 100 including, for example, the flow rate, the current pressure measurements, the actual displacement ($\delta y$) of the actuators 40, and the current life of the battery 60 via wireless signals 72 and 74 transmitted from and received by the RF transceiver 70. The disc pump system 100 may utilize a communications interface that comprises RF transceiver 70, infrared, or other wired or wireless signals to communicate with one or more external devices. The RF transceiver 70 may utilize Bluetooth, WiFi, WiMAX, or other communications standards or proprietary communications systems. Regarding the more specific uses, the RF transceiver 70 may send the signals 72 to a computing device that stores a database of pressure readings for reference by a medical professional. The computing device may be a computer, mobile device, or medical equipment device that may perform processing locally or further communicate the information to a central or remote computer for processing of the information and data. Similarly, the RF transceiver 70 may receive the signals 72 for externally regulating the pressure generated by the disc pump system 100 at the load 38 based on the motion of the actuators 40.

The driver 58 is an electrical circuit that energizes and controls the actuator 40. For example, the driver 58 may be a high-power transistor, amplifier, bridge, and/or filters for generating a specific waveform as part of the drive signals 64a, 64b. Such a waveform may be configured by the processor 56 and the driver 58 to provide drive signals 64a, 64b that cause the actuators 40 to vibrate in an oscillatory motion at the frequency (f), as described in more detail above. The oscillatory displacement motion of the actuators 40 generates the radial pressure oscillations of the fluid within the cavities of the disc pumps 10, 80 in response to the drive signals 64a, 64b to provide airflow and generate pressure at the load 38.

In another embodiment, the disc pump system 100 may include a user interface for displaying information to a user. The user interface may include a display, audio interface, or tactile interface for providing information, data, or signals to a user. For example, a miniature LED screen may display the pressure being generated by the disc pump system 100. The user interface may also include buttons, dials, knobs, or other electrical or mechanical interfaces for adjusting the performance of the disc pump, and particularly, the reduced pressure generated. For example, the pressure may be increased or decreased by adjusting a knob or other control element that is part of the user interface.

Enabling the measurement of a flow rate in the disc pump system 100 supplies a number of advantages. The flow rate of the disc pump system 100 can be measured without the need for additional components or expense, and a smaller footprint is required. In addition, the flow rate data can be used to determine conditions at the load 38. For example, the measured flow rate can be used to determine whether there is a leak at the load 38 and to collect data on the performance of the disc pump system 100.

In one embodiment, the disc pump system 100 determines whether there is a leak at the load 38 based on the measured flow rate and pressure. For example, the disc pump system 100 may determine that a leak at the load 38 exists if the flow rate at the pumps 10, 80 remains relatively constant over a time interval. In response to determining that a leak exists, the disc pump system 100 may shut down or transmit an alarm or alert signal via an audio interface. In one embodiment, in response to determining that a leak condition exists, the disc pump system 100 may conduct a diagnostic process to determine the cause of the leak. Such a process may include determining whether each of the pumps 10, 80 functions properly, and whether pressure is maintained at the load 38.

It should be apparent from the foregoing that an invention having significant advantages has been provided. While the invention is shown in only a few of its forms, it is not just limited but is susceptible to various changes and modifications without departing from the spirit thereof.

We claim:

1. A disc pump system comprising:
    a first disc pump having a first substantially cylindrical side wall closed at a first end by a first end wall to form a first cavity, and a first actuator formed by a first internal plate and supported within the first cavity by a first isolator extending between the first actuator and the first cylindrical side wall, the first disc pump configured to have a first specified flow rate and provide a first specified pressure differential;
    a second disc pump having a second substantially cylindrical side wall closed at a first end by a second end wall to form a second cavity, and a second actuator formed by a second internal plate and supported within the second cavity by a second isolator extending between the second actuator and the second cylindrical side wall, the second disc pump configured to have a second specified flow rate and provide a second specified pressure differential, the first specified flow rate being greater than the second specified flow rate and the first specified pressure differential being less than the second specified pressure differential; and
    a substrate having a known restriction, a second end of the first cylindrical side wall and a second end of the second cylindrical side wall mounted to the substrate, the first disc pump and the second disc pump being fluidly coupled by the known restriction.

2. The disc pump system of claim 1, further comprising a load, wherein the load is coupled to the substrate and fluidly coupled to the known restriction.

3. The disc pump system of claim 1, wherein the substrate is a printed circuit board.

4. The disc pump system of claim 1, wherein the known restriction has a tubular shape with a circular cross-section.

5. The disc pump system of claim 1, wherein the known restriction follows a tortuous path.

6. The disc pump system of claim 1, wherein the known restriction has a tubular shape with a circular cross section, and wherein the known restriction follows a tortuous path.

* * * * *